United States Patent
Akiyama et al.

(10) Patent No.: US 6,937,390 B2
(45) Date of Patent: Aug. 30, 2005

(54) OPERATION MICROSCOPE APPARATUS

(75) Inventors: Hiroshi Akiyama, Tokyo (JP);
Kazutoshi Takagi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 10/764,560

(22) Filed: Jan. 27, 2004

(65) Prior Publication Data

US 2004/0184142 A1 Sep. 23, 2004

(30) Foreign Application Priority Data

Jan. 30, 2003 (JP) .......... 2003-022832

(51) Int. Cl.⁷ .......... G02B 21/00
(52) U.S. Cl. .......... 359/381; 359/384; 351/216
(58) Field of Search .......... 359/368, 372–377, 359/381, 384, 817, 819, 822; 351/211, 212, 216

(56) References Cited

U.S. PATENT DOCUMENTS

| 4,807,989 A | * | 2/1989 | Nagano et al. .......... 351/212 |
| 5,793,524 A | * | 8/1998 | Luloh .......... 359/381 |
| 6,788,455 B2 | * | 9/2004 | Kirchhuebel et al. .......... 359/381 |

FOREIGN PATENT DOCUMENTS

| JP | 6-22980 | 2/1994 |
| JP | 2002-350735 | 12/2002 |

* cited by examiner

*Primary Examiner*—Mark A. Robinson
(74) *Attorney, Agent, or Firm*—Armstrong, Kratz, Quintos, Hanson & Brooks, LLP

(57) ABSTRACT

An operation microscope apparatus includes: an operation microscope (25) supported to a pillar through an electrically-operated elevating device for rough-motion (first upward-and-downward micro motion device 17); a lens support arm (51) supported to a support portion of the operation microscope (25) so as to be movable between a use position at which the lens support arm (51) is extended downward and a storage position at which the lens support arm (51) is stored upward; a front lens (74) held by the lens supported arm (51); a control unit for controlling the electrically-operated elevating device (arithmetic and control circuit 27); a switch for upward-and-downward rough-motion (30,31 or 94,95); and a detection unit for detecting a storage state of the lens support arm (51) to output a detection signal (microswitch 91). In the apparatus, only when the detection signal is received, the control unit (arithmetic and control circuit 27) controls the electrically-operated elevating device (first electrical upward-and-downward micro motion device 17) by operating the switch (30,31 or 94,95) to allow the operation microscope (25) to roughly move upward and downward.

3 Claims, 12 Drawing Sheets

OPERATION MICROSCOPE APPARATUS

BACKGROUND OF THE INVENTION

1. Field of the Invention

The present invention relates to an operation microscope apparatus which allows a front lens of an operation microscope to be disposed in front of an objective lens and which supports the operation microscope to an operation microscope support portion to enable upward and downward movement of the operation microscope by an electrically-operated elevating device.

2. Description of the Related Art

Up to now, there has been known an operation microscope system of a swing type in which a first arm is mounted on an upper end portion of a pillar so as to be horizontally rotatable, one end portion of a second arm (operation microscope support portion) is mounted to a free end portion of the first arm so as to be horizontally rotatable and swingable upward and downward, and an operation microscope is mounted to the other end portion of the second arm through an electrically-operated upward-and-downward micro-motion device (for example, JP laid-open No. 06-022980 A).

Also, there has been known an operation microscope in which a front lens is disposed in front of an objective lens of an observation optical system to observe an eye to be examined through the observation optical system and the front lens (for example, JP laid-open No. 2002-350735 A).

Now, when the operation microscope is not used in the above-mentioned operation microscope system, the operation microscope is substantially retreated upward from the vicinity of an observation region. In this case, if the front lens is disposed on the front side (lower side) of the objective lens, the front lens hinders the observation. Therefore, the front lens is supported by a holding arm such that the front lens can be removed from the front side (lower side) of the objective lens and retreated upward.

In such an apparatus for the operation microscope having the front lens, when the operation microscope is more roughly moved upward and downward with the front lens at a use position, it is necessary to sufficiently ensure the safety.

Here, "rough motion" means to be displaced roughly, "micro motion" means to be displaced finely.

SUMMARY OF THE INVENTION

Therefore, an object of the present invention is to provide an operation microscope apparatus capable of roughly moving an operation microscope upward and downward while securing sufficient safety.

In order to attain the above-mentioned object, according to an aspect of the present invention, there is provided an operation microscope apparatus including:

an operation microscope supported to a pillar through an electrically-operated elevating device;

a lens support arm supported to a support portion of the operation microscope so as to be movable between a use position at which the lens support arm is extended downward and a storage position at which the lens support arm is stored upward;

a front lens held by the lens support arm;

control means for controlling the electrically-operated elevating device;

a switch for upward-and-downward-rough-motion; and detection means for detecting a storage state of the lens support arm to output a detection signal, in which only when the detection signal of the storage state is received, the control means controls the electrically-operated elevating device by operating the switch to allow the operation microscope to move upward and downward.

Further, according to another aspect of the present invention, in the operation microscope apparatus, the lens support arm is supported to the support portion so as to be movable upward and downward within a predetermined area. In addition, according to another aspect of the present invention, the operation microscope apparatus further includes engaging means for engaging the lens support arm with the operation microscope at the storage position.

DETAILED DESCRIPTION OF THE PREFERRED EMBODIMENTS

Hereinafter, Embodiment 1 of the present invention will be described with reference to the drawings.

[Structure]

Figure 1:
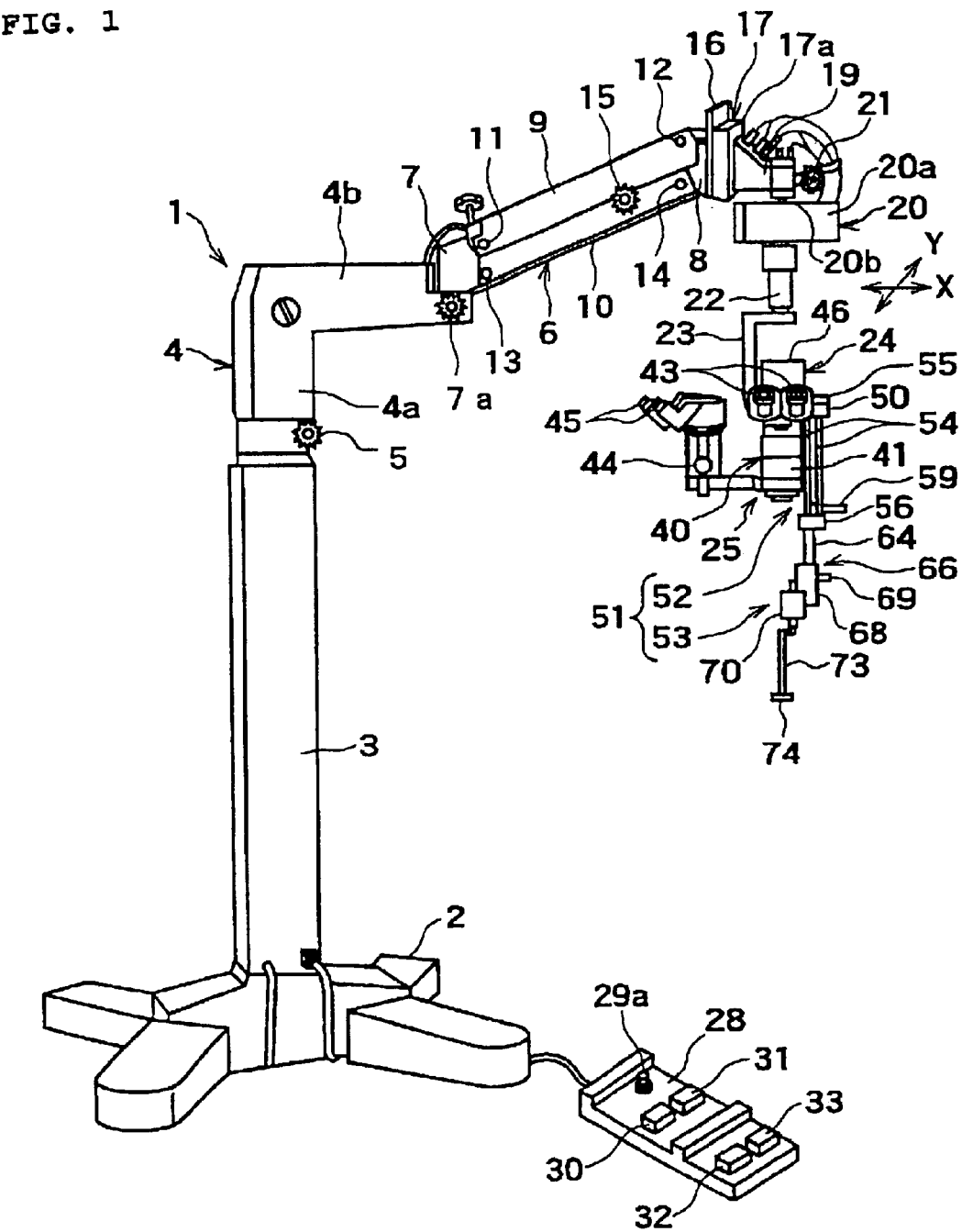
FIG. 1 is a perspective view showing an operation microscope apparatus according to Embodiment 1 of the present invention.

In FIG. 1, an operation microscope apparatus 1 includes: a support base 2; a pillar 3 integrally provided to the support base 2 in the upward-and-downward direction; and a first arm 4 mounted on an upper end portion of the pillar 3.

The first arm 4 is composed of a support portion 4a mounted to the upper end portion of the pillar 3 so as to be rotatable about a vertical rotation shaft (vertical shaft) and an arm portion 4b horizontally connected with the support portion 4a, and formed in a substantially L-shape. The support portion 4a is fixed to the upper end portion of the pillar 3 with a fixing screw 5.

A second arm (swing arm) 6 of a parallel link type includes: a first support member 7 which is mounted to a free end (tip) of the arm portion 4b of the first arm 4 so as to be horizontally rotatable about a rotation shaft (not shown) that extends upward and downward; a second support member 8 located at a distance from the first support member 7; and a pair of links 9 and 10 provided in parallel between the first support member 7 and the second support member 8. A rotation shaft (not shown) of the first support member 7 is fixed with a fixing screw 7a.

The second arm 6 includes: support shafts (lateral shafts) 11 and 12 that rotatably mount both end portions of the link 9 to the first support member 7 and the second support member 8; and support shafts (lateral shafts) 13 and 14 that rotatably mount both end portions of the link 10 to the first support member 7 and the second support member 8. According to the structure, the links 9 and 10 can be swung (rotated) upward and downward about the support shafts 11 and 13.

A rotatably urging member (not shown) that rotatably urges the links 9 and 10 upward is interposed between the links 9 and 10. The links 9 and 10 are rotated upward and downward and fixed at arbitrary positions with a fixing screw 15. Because known members can be employed for the structure, the detail description thereof is omitted here.

A vertically extending support plate (guide plate) 16 is fixed to the second support member 8. The support plate 16 holds a device main body 17a of a first electrically-operated upward-and-downward-motion device (electrically-operated elevating device) 17 that combines a rough-motion device and a micro-motion device in an upwardly and downwardly movable manner.

Figure 16:
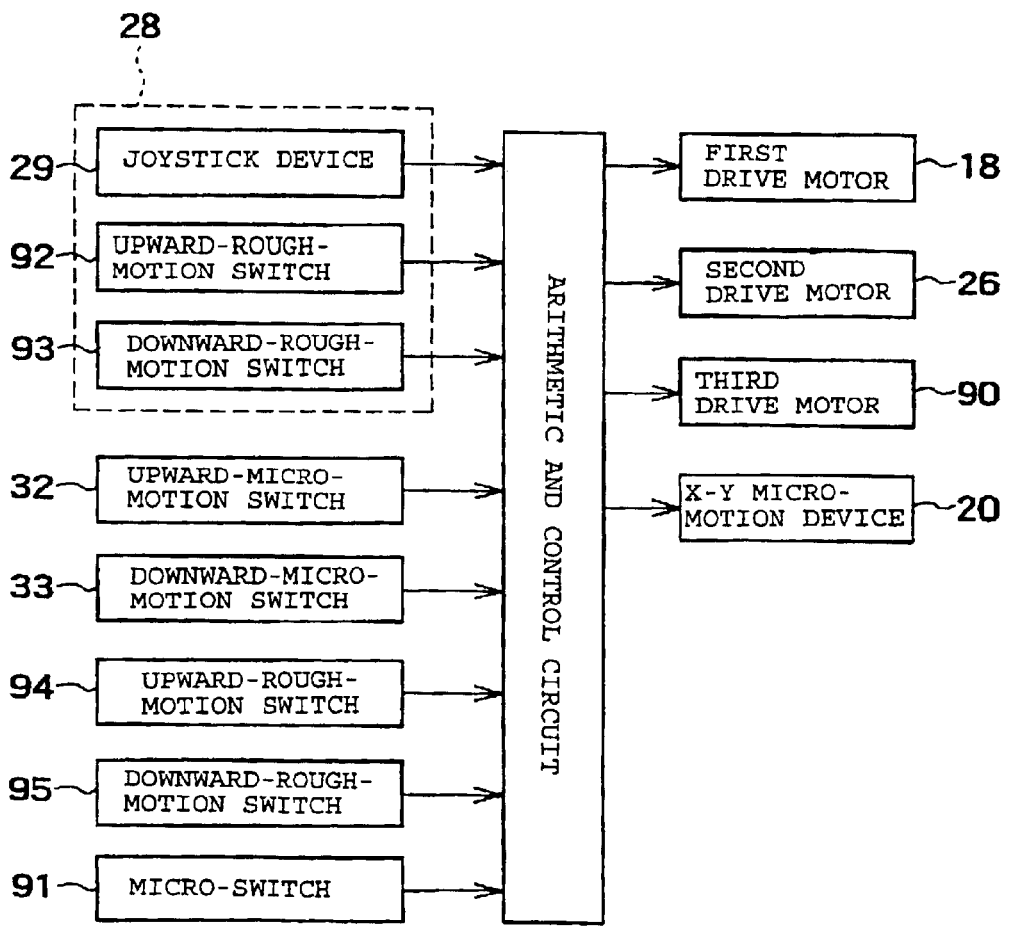
FIG. 16 is a control circuit diagram of the operation microscope apparatus shown in FIG. 8.

The device main body 17a incorporates a known micro-motion mechanism such as a feed mechanism utilizing a first drive motor 18 shown in FIG. 16 and a feed screw (not shown) rotated by the first drive motor 18 or a movable mechanism using the first drive motor 18 and a pinion and a rack which are rotated by the first drive motor 18.

A support member 19 is mounted to the device main body 17a. An X-Y micro-motion device (horizontal drive unit) 20 is located below the support member 19. The X-Y micro-motion device (horizontal drive unit) 20 includes a case 20a and a support shaft 20b integrally formed on the case 20a. The case 20a is mounted to the support member 19 through the support shaft 20b so as to be adjustable for horizontal rotation. The support shaft 20b is fixed to the support member 19 with a fixing screw 21.

The X-Y micro-motion device (horizontal drive unit) 20 can finely move an upwardly and downwardly extending support shaft 22 in the horizontal direction (X- and Y-directions). An L-shaped support bracket 23 is mounted to a lower end portion of the support shaft 22. A case main body 24a of a second electrically-operated upward-and-downward-motion device (electrically-operated elevating device) 24 for micro-motion is mounted to a lower end portion of the support bracket (microscope support portion) 23 (see FIGS. 1 and 2A).

The case main body 24a incorporates a known micro-motion mechanism such as a feed mechanism utilizing a second drive motor 26 shown in FIG. 16 and a feed screw (not shown) rotated by the second drive motor 26 or a movable mechanism using the second drive motor 26 and a pinion and a rack which are rotated by the second drive motor 26.

An operation microscope 25 is located below the second electrically-operated upward-and-downward-motion device (electrically-operated upward-and-downward-micro-motion device) 24. The operation microscope 25 includes a microscope main body 40. The microscope main body 40 has a lens body tube 41 located at one end and a housing portion 42 which is connected with the lens body tube 41 and incorporates an illumination device. Eyepieces 43, 43 for an operator are provided to an upper end portion of the lens body tube 41 (see FIG. 1).

An observation optical system which is not shown is provided in a section from the lens body tube 41 to the eyepieces 43, 43. Note that an objective lens which is not shown is located within a lower end portion of the lens body tube 41.

Figures 2A, 2B:
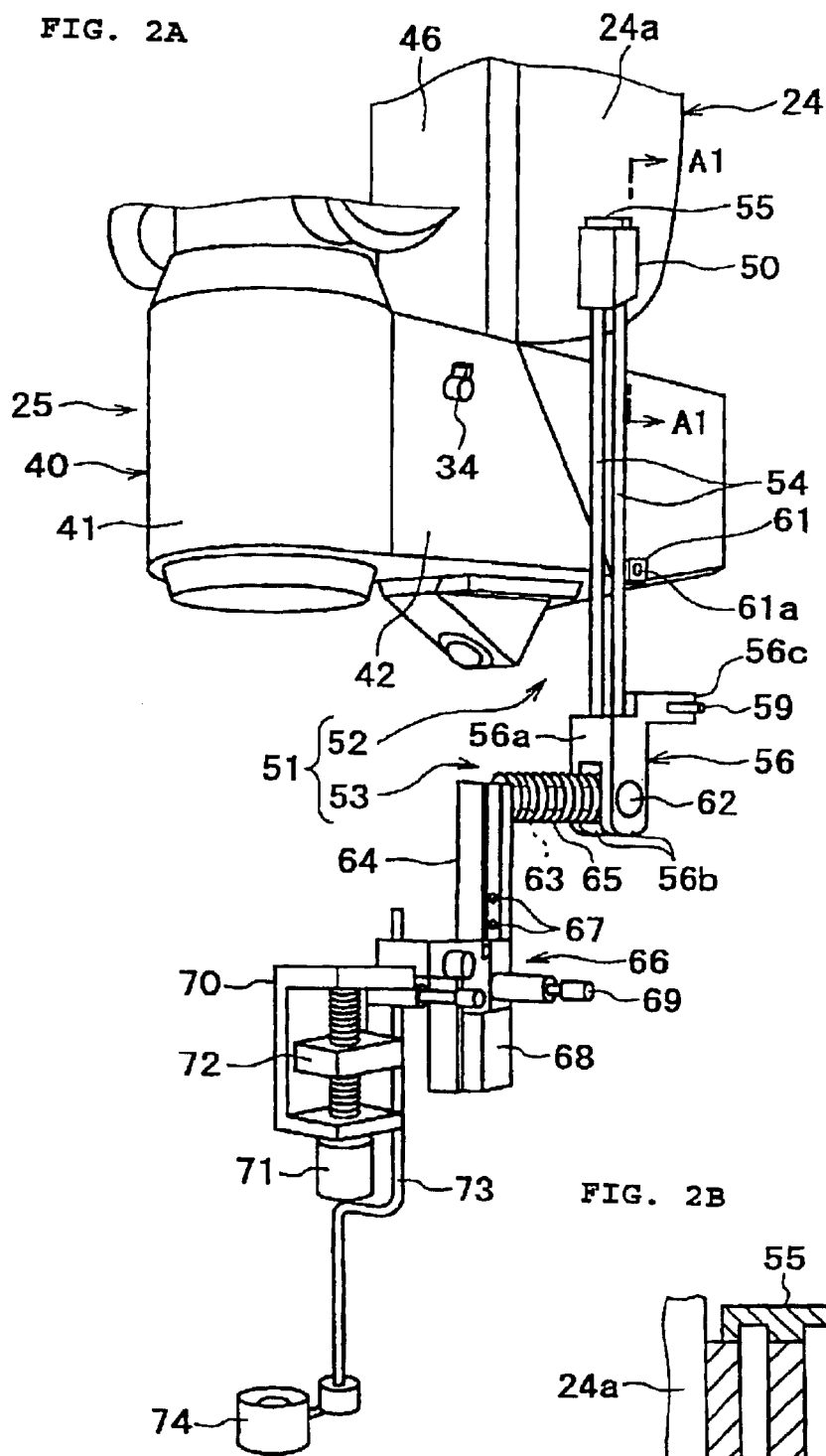
FIG. 2A is an enlarged perspective view showing a lens support arm shown in FIG. 1
FIG. 2B is a cross sectional view taken along a line A1—A1 shown in FIG. 2A.

As shown in FIG. 1, a lens body tube 44 and eyepieces 45, 45, which are provided for an assistant are attached to one side surface of the microscope main body 40. Further, as shown in FIG. 2A, a support plate 46 is integrally provided on an upper center end portion of the microscope main body 40 in a direction in which the lens body tube 41 and the housing portion 42 are arranged. The second electrically-operated upward-and-downward-motion device 24 holds the support plate 46 in an upwardly and downwardly movable manner.

<Lens Support Arm>

A shaft guide member 50 that extends upward and downward is fixed to the other side surface of the microscope main body 40 by a fixing member which is not shown. As shown in FIG. 2B, a pair of shaft guide holes 50a, 50b which penetrate vertically and are provided parallel to each other are formed in the shaft guide member 50. A lens support arm 51 is held to the shaft guide member 50.

As shown in FIGS. 1 to 5, the lens support arm 51 includes: an upper arm portion 52 that extends upward and downward; and a lower arm portion 53 whose one end is held to a lower end of the upper arm portion 52 so as to be foldable in a direction along the upper arm portion 52.

(Upper Arm Portion 52)

As shown in FIG. 2A, the upper arm portion 52 includes: a pair of support shafts 54, 54 which are inserted into the pair of shaft guide holes 50a and 50b of the shaft guide member 50 without any play in an upwardly and downwardly movable manner; a connecting and fixing member 55 that integrally fixes upper end portions of the support shafts 54, 54; and an inverse U-shaped connecting and fixing member 56 that integrally fixes lower end portions of the support shafts 54, 54.

The connecting and fixing member 56 is composed of a connecting portion 56a that integrally fixes the lower end portions of the support shafts 54, 54 and a pair of opposite support segments 56b, 56b which are provided to protrude downward inversely U-shaped from the connecting portion 56a. When the lens body tube 41 side is assumed to be a front side and the housing portion 42 side is assumed to be a rear side, a mounting segment 56c that extends rearward along a side surface of the housing portion 42 is integrally provided to the connecting portion 56a. Note that the support segments 56b, 56b are provided on the rear side with a distance therebetween. A portion of the connecting portion 56a is located below the housing portion 42 so as to approximate the lower arm portion 53 to a space below the microscope main body 40.

Figure 6:
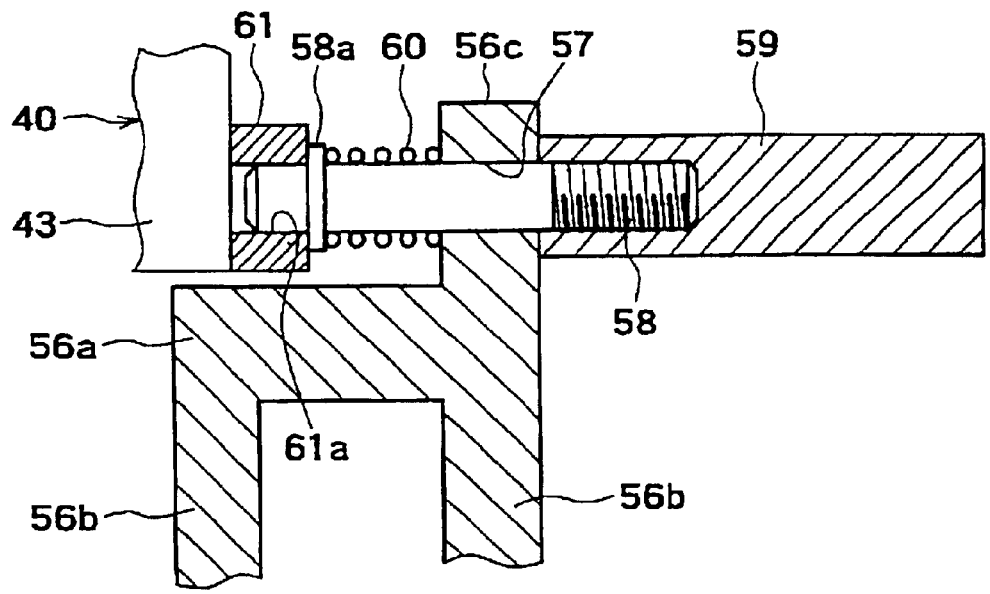
FIG. 6 is a cross sectional view taken along a line A2—A2 shown in FIG. 4.
Figure 7:
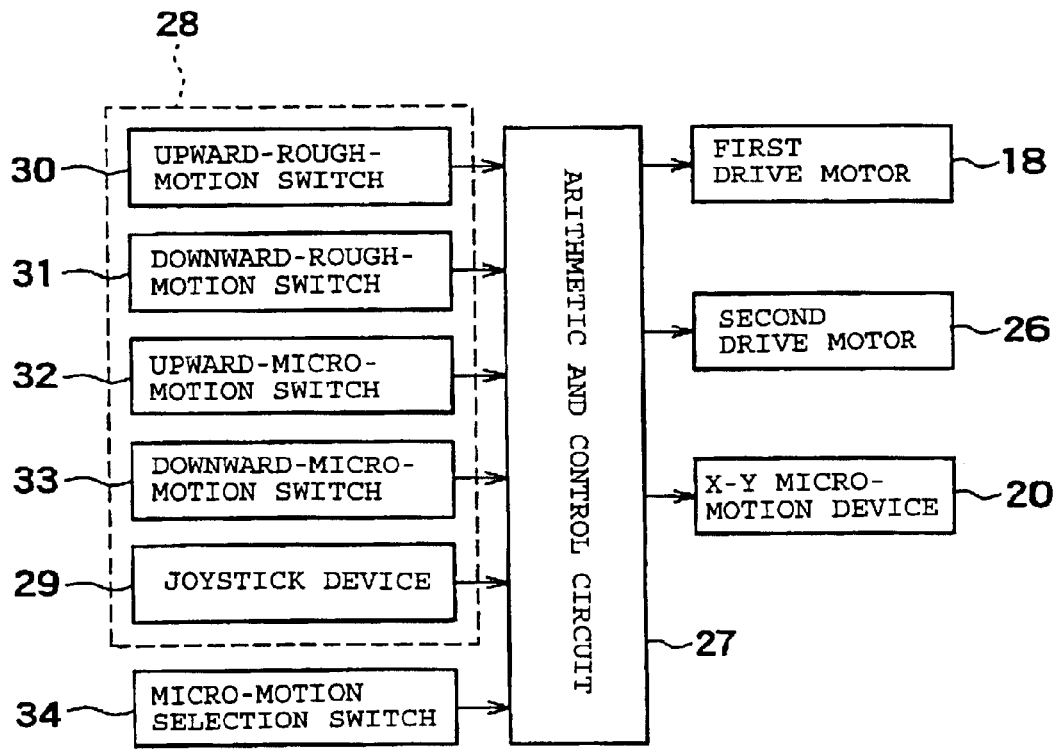
FIG. 7 is a control circuit diagram of the operation microscope apparatus shown in FIG. 1.
Figure 8:
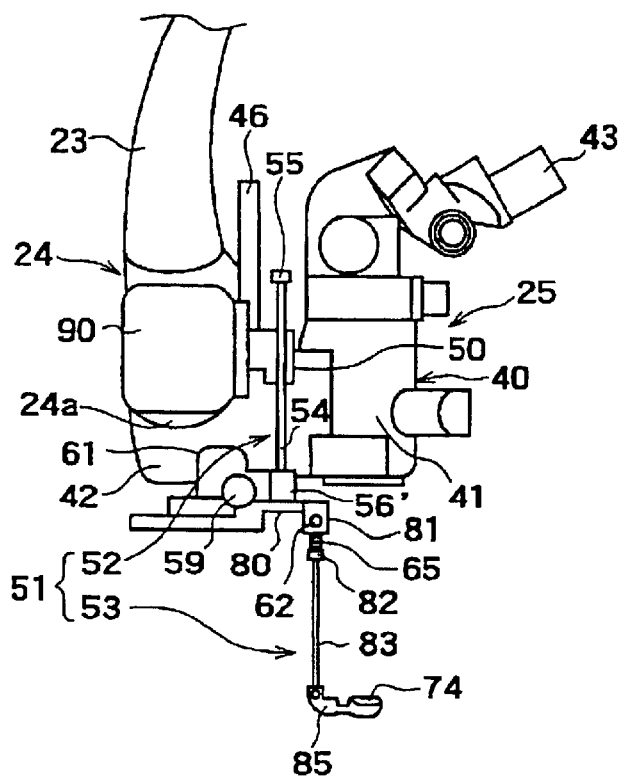
FIG. 8 is a partial side view showing an operation microscope apparatus according to Embodiment 2 of the present invention.

As shown in FIG. 6, a shaft through hole 57 that extends in a direction orthogonal to the side surface of the housing portion 42 is formed in the mounting segment 56c. An engaging pin 58 serving as a member to be engaged is inserted through the shaft through hole 57. An operating shaft 59 which is located on an opposite side to the housing portion 42 with respect to the engaging pin 58 is screwed as an operating knob (operating portion) to an end portion of the engaging pin 58.

A flange 58a is formed to a middle portion of the engaging pin 58. A coil spring 60 serving as an urging member is interposed between the flange 58a and the mounting segment 56c. The coil spring 60 urges the engaging pin 58 to the housing portion 42 side, so that a tip portion of the engaging pin 58 protrudes below the housing portion 42.

An engaging plate 61 which is located at a lower end of the side surface of the housing portion 42 on the upper arm portion 52 side is mounted as an engaging member to the housing portion 42. An engaging hole 61a is formed as an engaging portion in the engaging plate 61. When the operating shaft 59 is pulled against the spring force of the coil spring 60, the engaging pin 58 integrated with the operating shaft 59 is detached from below the housing portion 42 and below the engaging plate 61 to the side.

When the operating shaft 59 is pulled against the spring force of the coil spring 60 to detach the engaging pin 58 from below the engaging plate 61 to the side and the operating shaft 59 is lifted up in this state, the entire upper arm portion 52 can be lifted up to the side of the engaging plate 61. In addition, the tip portion of the engaging pin 58 can be opposed to the engaging hole 61a by the lifting operation. At this opposite position, the tip portion of the engaging pin 58 can be inserted into the engaging hole 61a.

(Lower Arm Portion 53)

The lower arm portion 53 includes: a rotation shaft 62 having both end portions thereof being rotatably held to the support segments 56b, 56b of the connecting and fixing member 56; a connecting shaft 63 in which one end portion thereof is integrally provided to the rotation shaft 62; a guide shaft 64 which is provided orthogonal (vertical) to the connecting shaft 63 and mounted to the connecting shaft 63 so as to be rotatable about an axis of the connecting shaft 63; and a coil spring (urging member) 65 which is fitted to the circumference of the connecting shaft 63 and interposed between the guide shaft 64 and the support segments 56b, 56b. The rotation shaft 62 extends in a direction orthogonal to the side surface of the microscope main body 40 (lateral direction).

Note that, when the connecting shaft 63 becomes orthogonal (vertical) to the front surface or the rear surface of the support segments 56b, 56b, the coil spring 65 has two functions, that is, a function for holding the connecting shaft 63 so as to be orthogonal (vertical) to the front surface or the rear surface of the support segments 56b, 56b and a function for holding the guide shaft 64 to the connecting shaft 63 by friction.

A manual rough-motion adjusting mechanism 66 is attached to the guide shaft 64. The rough-motion adjusting mechanism 66 includes: a plurality of engaging holes 67 which are provided to the guide shaft 64 in a longitudinal direction (sliding direction) at a distance; a cylindrical sliding member 68 which is fitted to the guide shaft 64 so as to be adjustable for movement in its axis direction; and an engaging shaft 69 which is held to the sliding member 68 and provided so as to be insertable into and removable from one of the plurality of engaging holes 67.

A manual micro-motion mechanism (micro-adjusting mechanism) 70 is mounted to the sliding member 68. The micro-motion mechanism 70 includes a sliding member 72 that finely moves in the moving direction of the sliding member 68 by the rotational operation of an operating shaft 71.

A cranked support arm (bent arm portion) 73 is provided to the sliding member 72. A front lens 74 is mounted to a tip portion of the support arm 73. As shown in FIGS. 1 and 2A, when the lower arm portion 53 is extended downward, the support arm 73 is located below the housing portion 42 and the front lens 74 is located below the objective lens.

The first and second drive motors 18 and 26 are controlled in accordance with drive pulses from an arithmetic and control circuit (control unit) 27. The X-Y micro-motion device 20 and the first and second drive motors 18 and 26 can be operated by a foot operation device 28.

The foot operation device 28 includes a joystick device 29. The joystick device 29 has a joystick 29a tiltable for operation in an arbitrary direction. A tilt operation signal of the joystick 29a is inputted from the joystick device 29 to the arithmetic and control circuit 27. The arithmetic and control circuit 27 causes the support shaft 22 to finely move in the X- and Y-directions in accordance with the tilt operation signal from the joystick device 29.

Also, the foot operation device 28 includes an upward-rough-motion switch 30, a downward-rough-motion switch 31, an upward-micro-motion switch 32, and a downward-micro-motion switch 33. A micro-motion selection switch 34 for selectively operating the first and second electrically-operated upward-and-downward-motion devices 17 and 24 when the upward-micro-motion switch 32 or the downward-micro-motion switch 33 is operated is provided to a side portion of the microscope main body 40. Operation signals from the respective switches 30 to 34 are inputted to the arithmetic and control circuit 27.

When the operation signal from the upward-micro-motion switch 32 is inputted in a state in which the first electrically-operated upward-and-downward-motion device 17 is selected by the micro-motion selection switch 34, the arithmetic and control circuit 27 controls the first drive motor 18 of the first electrically-operated upward-and-downward-motion device 17 to finely move the operation microscope 25 upward. In addition, when the operation signal from the downward-micro-motion switch 33 is inputted in the state in which the first electrically-operated upward-and-downward-motion device 17 is selected by the micro-motion selection switch 34, the arithmetic and control circuit 27 controls the first drive motor 18 of the first electrically-operated upward-and-downward-motion device 17 to finely move the operation microscope 25 downward.

When the operation signal from the upward-micro-motion switch 32 is inputted in a state in which the second electrically-operated upward-and-downward-motion device 24 is selected by the micro-motion selection switch 34, the arithmetic and control circuit 27 controls the second drive motor 26 of the second electrically-operated upward-and-downward-motion device 24 to finely move the operation microscope 25 upward. In addition, when the operation signal from the downward-micro-motion switch 33 is inputted in the state in which the second electrically-operated upward-and-downward-motion device 24 is selected by the micro-motion selection switch 34, the arithmetic and control circuit 27 controls the second drive motor 26 of the second electrically-operated upward-and-downward-motion device 24 to finely move the operation microscope 25 downward.

Further, when the operation signal from the upward-rough-motion switch 30 is inputted, the arithmetic and control circuit 27 controls the first drive motor 18 of the first electrically-operated upward-and-downward-motion device 17 to finely move the support member 19 upward with respect to the second arm 6 and controls the second drive motor 26 of the second electrically-operated upward-and-downward-motion device 24 to finely move the operation microscope 25 upward with respect to the support bracket 23. As a result, the operation microscope 25 roughly moves roughly upward with respect to the second arm 6.

In addition, when the operation signal from the downward-rough-motion switch 31 is inputted, the arithmetic and control circuit 27 controls the first drive motor 18 of the first electrically-operated upward-and-downward-motion device 17 to finely move the support member 19 downward with respect to the second arm 6 and controls the second drive motor 26 of the second electrically-operated upward-and-downward-motion device 24 to finely move the operation microscope 25 downward with respect to the support bracket 23. As a result, the operation microscope 25 roughly moves downward with respect to the second arm 6.

[Operation]

Next, the operation of the operation microscope apparatus having the above-mentioned structure will be described.

<Rough Position Adjustment>

In the structure, the lower arm portion 53 of the lens support arm 51 extends downward, so that the front lens 74 is located below the objective lens of the observation optical system which is not shown, of the microscope main body 40.

The fixing screw 5 is loosened and the arm portion 4b of the first arm 4 is horizontally rotated, so that the second arm 6 can be roughly turned in a target direction. After the second arm 6 is thus roughly turned in the target direction, the fixing screw 5 is tightened to fix (lock) the first arm 4 so as not to be horizontally rotated.

In this state, the fixing screws 7a and 15 are loosened and the operation microscope 25 is held by the operator and moved from right to left or up and down, thereby horizontally rotating the second arm 6 about the rotation shaft (not shown) of the first support member 7 while being swung upward and downward. Accordingly, the operation microscope 25 can be moved to a target location. In addition, when the fixing screw 21 is loosened, the operation microscope 25 can be rotated together with the support shaft 20b about its axis. Therefore, an orientation of the operation microscope 25 in the horizontal direction can be changed by its rotation.

By the above-mentioned operation, when the operation microscope 25 and the front lens 74 are moved to a position at which a surgical region can be roughly observed and the fixing screws 7a, 15, and 21 are tightened, the rough position setting of the operation microscope 25 is completed.

In this state, when an operator tilts the joystick 29a of the foot operation device 28, a tilt operation signal from the joystick 29a is inputted to the arithmetic and control circuit 27. The arithmetic and control circuit 27 controls the X-Y micro-motion device 20 to finely move the support shaft 22 in the same direction as the tilt direction of the joystick 29a. When the operator tilts the joystick 29a to drive the support shaft 22 in the horizontal direction, the operation microscope 25 supported by the support shaft 22 is finely moved in the horizontal direction. Therefore, the adjustment is performed such that the entire target surgical region (for example, an anterior segment of an eye to be examined) is located within a field of view of the operation microscope 25.

<Focusing Operation>

When the rough position adjustment in the upward-and-downward direction is insufficient even after the above-mentioned adjustment, the operator selectively operates the upward-rough-motion switch 30 and the downward-rough-motion switch 31, so that an operation signal from the upward-rough-motion switch 30 or the downward-rough-motion switch 31 is inputted to the arithmetic and control circuit 27.

When the operation signal from the upward-rough-motion switch 30 or the downward-rough-motion switch 31 is inputted, the arithmetic and control circuit 27 controls the first drive motor 18 of the first electrically-operated upward-and-downward-motion device 17 to finely move the support member 19 upward or downward at a speed v1 with respect to the second arm 6. In addition, the arithmetic and control circuit 27 controls the second drive motor 26 of the second electrically-operated upward-and-downward-motion device 24 to finely move the operation microscope 25 upward or downward at a speed v2 with respect to the support bracket 23. As a result, the operation microscope 25 is roughly moved upward or downward at a speed (v1+v2) with respect to the second arm 6. At this time, if v1=v2, the operation microscope 25 is roughly moved upward or downward at a speed 2v1.

Therefore, the operation microscope 25 and the front lens 74 are roughly moved upward and downward with respect to an observation region (surgical region) such as an eye of a person to be examined, so that the operation microscope 25 and the front lens 74 are roughly adjusted in the upward-and-downward direction with respect to the observation region.

After that, the operator selects the first electrically-operated upward-and-downward-motion device 17 or the second electrically-operated upward-and-downward-motion device 24 by using the micro-motion selection switch 34 and selectively operates the upward-micro-motion switch 32 and the downward-micro-motion switch 33.

In the case where the first electrically-operated upward-and-downward-motion device 17 is selected by the micro-motion selection switch 34, when the operation signal from the upward-micro-motion switch 32 is inputted, the arithmetic and control circuit 27 controls the first drive motor 18 of the first electrically-operated upward-and-downward-motion device 17 to finely move the operation microscope 25 and the front lens 74 upward integrally. In addition, in the case where the first electrically-operated upward-and-downward-motion device 17 is selected by the micro-motion selection switch 34, when the operation signal from the downward-micro-motion switch 33 is inputted, the arithmetic and control circuit 27 controls the first drive motor 18 of the first electrically-operated upward-and-downward-motion device 17 to finely move the operation microscope 25 and the front lens 74 downward integrally.

In the case where the second electrically-operated upward-and-downward-motion device 24 is selected by the micro-motion selection switch 34, when the operation signal from the upward-micro-motion switch 32 is inputted, the arithmetic and control circuit 27 controls the second drive motor 26 of the second electrically-operated upward-and-downward-motion device 24 to finely move the operation microscope 25 upward with respect to the front lens 74. In addition, in the case where the second electrically-operated upward-and-downward-motion device 24 is selected by the micro-motion selection switch 34, when the operation signal from the downward-micro-motion switch 33 is inputted, the arithmetic and control circuit 27 controls the second drive motor 26 of the second electrically-operated upward-and-downward-motion device 24 to finely move the operation microscope 25 downward with respect to the front lens 74.

Therefore, the operator selectively operates the upward-micro-motion switch 32 and the downward-micro-motion switch 33 to finely move the operation microscope 25 and the front lens 74 upward and downward integrally to finely move the operation microscope 25 relative to the front lens 74 upward and downward. Thus, the focusing operation of the operation microscope 25 to the observation region (surgical region) is performed. Then, in a state in which the focusing operation had been performed, the operator conducts surgery while observing the surgical region by using the operation microscope 25.

<Folding of Lens Support Arm 51>

When the front lens 74 is not used during the surgery, the lower arm portion 53 of the lens support arm 51 is backwardly turned about the rotation shaft 62, so that the connecting shaft 63 is located on the rear side of the support segments 56b, 56b of the connecting and fixing member 56.

Figure 3:
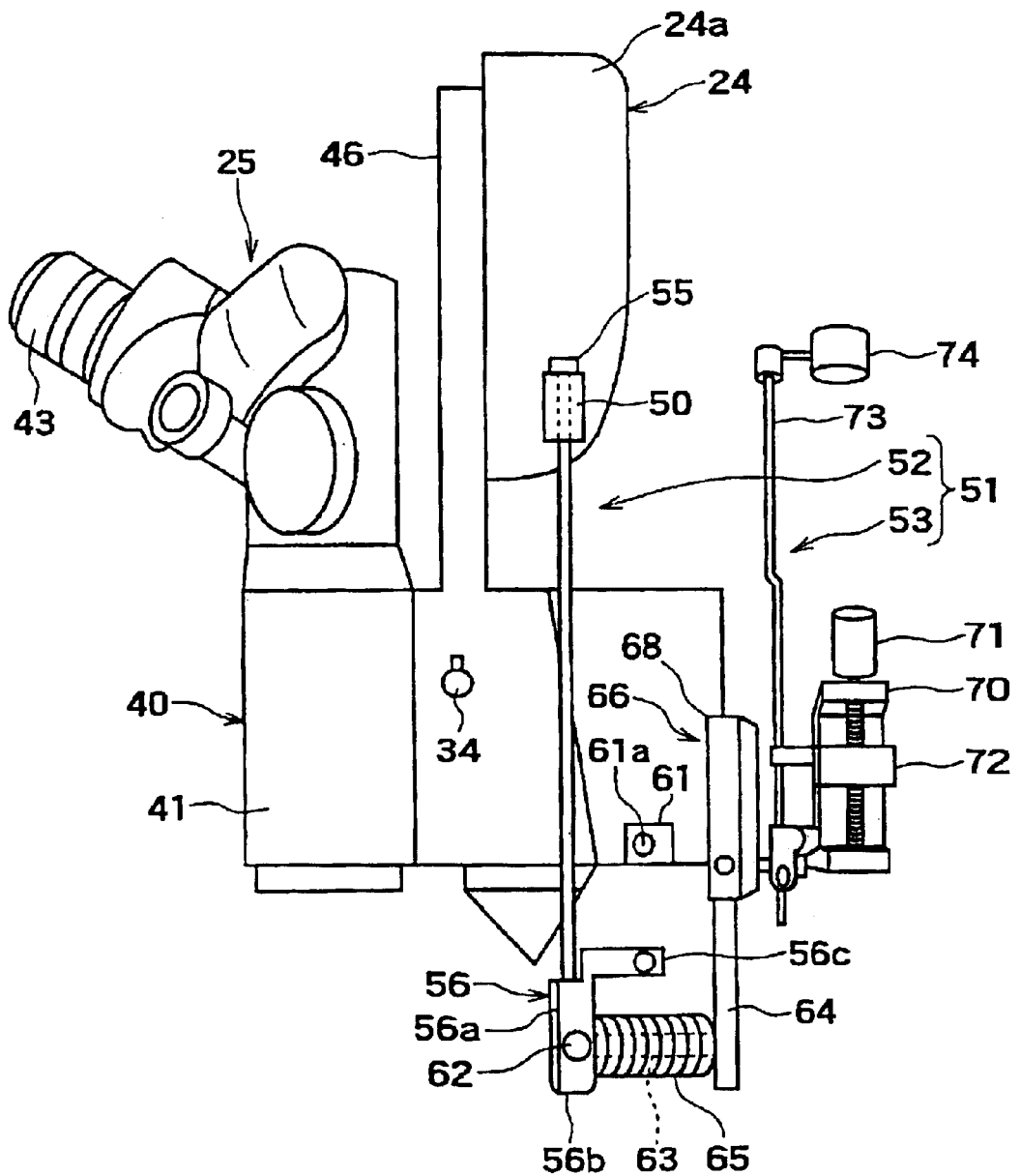
FIG. 3 is a partially enlarged side view in a state in which the lens support arm shown in FIGS. 1 and 2A is folded.

Then, the guide shaft 64 is upwardly rotated about the connecting shaft 63, so that the lower arm portion 53 can be upwardly folded along the upper arm portion 52 as shown in FIG. 3.

In this state, the operating shaft 59 is pulled against the spring force of the coil spring 60 to detach the engaging pin 58 from below the engaging plate 61 to the side and the operating shaft 59 is lifted up. At this time, the support shafts 54, 54 of the upper arm portion 52 are guided by the shaft guide member 50 and lifted up relative to the second electrically-operated upward-and-downward-motion device 24. Thus, the entire upper arm portion 52 is lifted up to the side of the engaging plate 61. The tip portion of the engaging pin 58 is opposed to the engaging hole 61a by the lifting operation and then the tip portion of the engaging pin 58 can be inserted into the engaging hole 61a.

Figure 4:
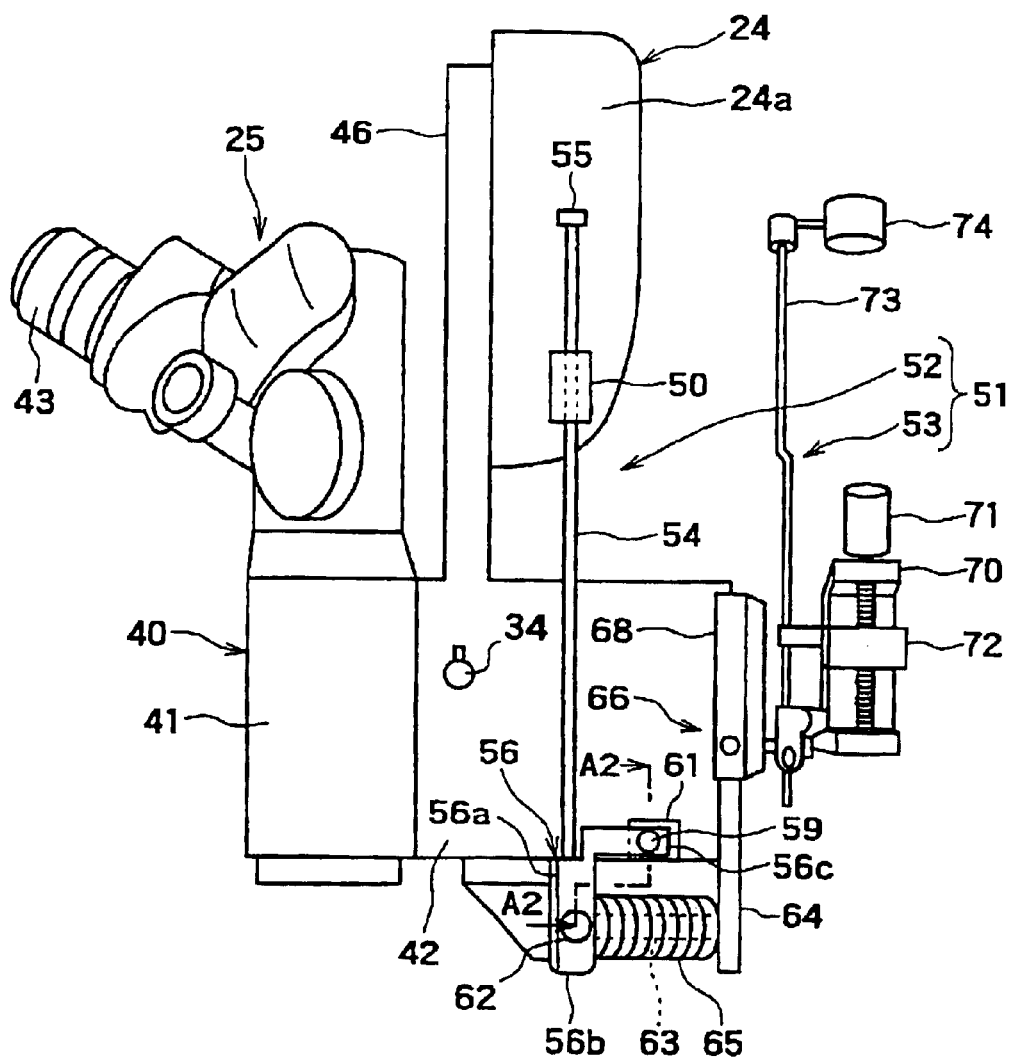
FIG. 4 is a partially enlarged side view in a state in which the lens support arm shown in FIG. 3 is engaged with an operation microscope.
Figure 5:
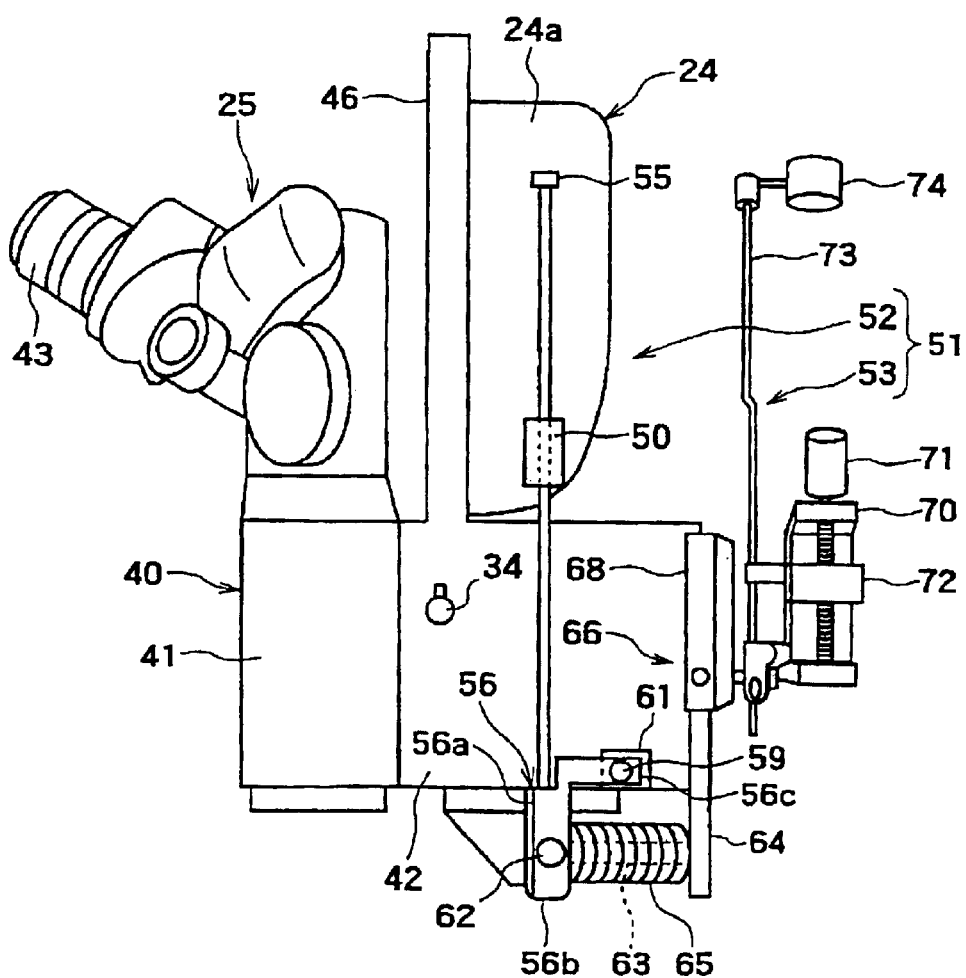
FIG. 5 is a partially enlarged side view when the operation microscope shown in FIG. 4 is maximally moved upward by a second micro-motion device.

According to the above-mentioned operation, in a state in which a side portion of the connecting and fixing member 56 is located closest to the lower end of the housing portion 42, the lens support arm 51 is engaged with the operation microscope 25 as shown in FIG. 4. Therefore, there is no case where the connecting and fixing member 56 protrudes significantly downward from the operation microscope 25. Thus, it is possible to prevent the lens support arm 51 from hindering the surgery or the like when the front lens 74 is not used.

<Retreat Rough-motion Operation>

On the other hand, during the surgery, when the operation microscope 25 is moved significantly upward from the vicinity of the surgical region to substantially retreat the operation microscope 25 upward from the vicinity of the surgical region, the operator operates the upward-rough-motion switch 30 to input the operation signal from the upward-rough-motion switch 30 to the arithmetic and control circuit 27.

When the operation signal from the upward-rough-motion switch 30 is inputted, the arithmetic and control circuit 27 controls the first drive motor 18 of the first electrically-operated upward-and-downward-motion device 17 to finely move the support member 19 upward at the speed v1 with respect to the second arm 6. In addition, the arithmetic and control circuit 27 controls the second drive motor 26 of the second electrically-operated upward-and-downward-motion device 24 to finely move the operation microscope 25 upward at the speed v2 with respect to the support bracket 23. As a result, the operation microscope 25 is roughly moved upward at the speed (v1+v2) with respect to the second arm 6. At this time, if v1=v2, the operation microscope 25 is roughly moved upward at the speed 2v1.

Also, when the second drive motor 26 of the second electrically-operated upward-and-downward-motion device 24 is controlled to finely move the operation microscope 25 upward at the speed v2 with respect to the support bracket 23, the lens support arm 51 is lifted up together with the operation microscope 25 integrally. Thus, when the operation microscope 25 is maximally moved upward by the first electrically-operated upward-and-downward-motion device 17 and the second electrically-operated upward-and-downward-motion device 24, the operation microscope 25 and the lens support arm 51 can be retreated to an upward retreat position (see FIG. 5).

The above-mentioned upward-rough-motion control of the operation microscope 25 may be performed by the arithmetic and control circuit 27 only for the period in which the upward-rough-motion switch 30 is pressed.

After the upward-rough-motion switch 30 is pressed once, even if the upward-rough-motion switch 30 is continued to be pressed, the arithmetic and control circuit 27 may control the first drive motor 18 and the second drive motor 26 to lift up the operation microscope 25 to its maximum.

<Downward-rough-motion Operation>

When the operation microscope 25 which is at the retreat position as described above is to be returned to the observation position near the surgical region, the operator operates the downward-rough-motion switch 31 to input the operation signal from the downward-rough-motion switch 31 to the arithmetic and control circuit 27.

When the operation signal from the downward-rough-motion switch 31 is inputted, the arithmetic and control circuit 27 controls the first electrically-operated upward-and-downward-motion device 17 to finely move the support member 19 downward with respect to the second arm 6. In addition, the arithmetic and control circuit 27 controls the second electrically-operated upward-and-downward-motion device 24 to finely move the operation microscope 25 downward with respect to the support bracket 23. As a result, the operation microscope 25 is roughly moved downward with respect to the second arm 6.

At this time, the arithmetic and control circuit 27 is set to control so as to roughly move the operation microscope 25 downward by the amount corresponding to the upward-rough-motion, thereby return the operation microscope 25 to a position at which the observation region can be observed.

That is, when the operation microscope 25 is roughly moved upward to be retreated, the number of drive pulses of the first drive motor 18 of the first electrically-operated upward-and-downward-motion device 17 and the number of drive pulses of the second drive motor 26 of the second electrically-operated upward-and-downward-motion device 24, which are used for the rough-motion, are stored in a memory (not shown) by the arithmetic and control circuit 27. This storage operation can be performed by providing a storage switch or the like. When the operation signal from the downward-rough-motion switch 31 is inputted, the arithmetic and control circuit 27 reads out from the memory (not shown) the number of drive pulses of the first drive motor 18 and the second drive motor 26, which are used for the upward-rough-motion. The first drive motor 18 and the second drive motor 26 are reversely rotated as compared with the upward-rough-motion by the number of drive pulses read out. Therefore, the operation microscope 25 is set roughly to move downward by the amount corresponding to the upward-rough-motion, thereby returning the operation microscope 25 to a position at which the surgical region can be observed.

Then, when the operating shaft 59 is pulled against the spring force of the coil spring 60, the tip portion of the engaging pin 58 can be taken out from the engaging hole 61a and the lens support arm 51 is downwardly moved relative to the operation microscope 25. At this time, the support shafts 54, 54 are guided by the shaft guide member 50 and moved downward. The connecting and fixing member 55 is moved downward until coming in contact with an upper end of the shaft guide member 50.

Next, when the guide shaft 64 is downwardly turned about the connecting shaft 63 and the lower arm portion 53 is forwardly turned about the rotation shaft 62, the lower arm portion 53 extends downward and the front lens 74 is set to be located below the objective lens of the observation optical system of the operation microscope 25.

As described above, the operation microscope 25 moves on the same axis in the vertical direction by the first electrically-operated upward-and-downward-motion device 17 with respect to the upward-and-downward direction.

In Embodiment 1 of the present invention, a detection unit (storage detection unit) such as a switch or a sensor may be provided for detecting the above-mentioned folding state of the lens support arm 51 and a storage state in which the side portion of the connecting and fixing member 56 is closest to the lower end of the housing portion 42 and the lens support arm 51 is engaged with the operation microscope 25 as shown in FIG. 4. Then, it may be constructed such that the above-mentioned rough-motion operation can be performed by the first and second electrically-operated upward-and-downward-motion devices 17 and 24 only when a detection signal from the detection unit is inputted to the arithmetic and control circuit 27. The rough-motion operation may be performed by only the first electrically-operated upward-and-downward-motion device 17.

<Setting for Upward-rough-motion of Front Lens to Use Position>

While the lens support arm 51 is folded and the tip portion of the engaging pin 58 is inserted into the engaging hole 61*a*, the lens support arm 51 and the front lens 74 are in the stored state and set the front lens 74 in the unused state, the operation of the eye to be examined or the like may happen to be conducted. In the above-mentioned states, the operation microscope 25 is located closer to the eye to be examined as compared with the case when the front lens 74 is used.

Therefore, when the surgery under the above-mentioned states is changed to the surgery using the front lens 74, the following setting for controlling the first electrically-operated upward-and-downward-motion device 17 is also possible.

That is, setting is made such that the first electrically-operated upward-and-downward-motion device 17 can be used as the rough-motion device. In addition, the first electrically-operated upward-and-downward-motion device 17 is controlled by the arithmetic and control circuit 27 such that the upward-rough-motion can be performed by the predetermined amount up to a position at which the front lens 74 can be used when the upward-rough-motion switch 30 is pressed.

According to the structure employing the above-mentioned setting operation, when the surgery which is conducted using the operation microscope 25 without using the front lens 74 while the observation region (surgical region) such as the eye to be examined is observed is changed to the surgery using the front lens 74, the upward-rough-motion switch 30 maybe pressed. Thus, the arithmetic and control circuit 27 controls the first electrically-operated upward-and-downward-motion device 17 to roughly move the X-Y micro-motion device 20, the support shaft 22, the support bracket 23, the second electrically-operated upward-and-downward-motion device 24, and the operation microscope 25 upward integrally by the predetermined amount. Therefore, the operation microscope 25 is upwardly moved up to a position at which the lens support arm 51 can be extended downward. By this extending, the front lens 74 is located below the objective lens (not shown) of the operation microscope 25, so that the surgery can be conducted while the observation region (surgical region) such as the eye to be examined is observed using the operation microscope 25 and the front lens 74.

When the surgery using the front lens 74 is changed into the observation using the operation microscope 25 without using the front lens 74, the lens support arm 51 is folded and the tip portion of the engaging pin 58 is inserted into the engaging hole 61*a*, with the result that the lens support arm 51 and the front lens 74 are each in the storage state and the front lens 74 is in the unused state. Then, the downward-rough-motion switch 31 is pressed. Thus, the arithmetic and control circuit 27 controls the first electrically-operated upward-and-downward-motion device 17 to roughly move the X-Y micro-motion device 20, the support shaft 22, the support bracket 23, the second electrically-operated upward-and-downward-motion device 24, and the operation microscope 25 downward integrally by the predetermined amount. Therefore, the operation microscope 25 is downwardly moved to a position at which the surgery can be conducted while the observation region (surgical region) such as the eye to be examined is observed using only the operation microscope 25.

According to the structure employing the above-mentioned control operation, a stroke produced in the upward-rough-motion operation or the downward-rough-motion operation to the X-Y micro-motion device 20, the support shaft 22, the support bracket 23, the second electrically-operated upward-and-downward-motion device 24, and the operation microscope 25, and the like becomes smaller than a stroke produced at a time when the members are more significantly retreated or returned. As a result, a small size device can be used as the first electrically-operated upward-and-downward-motion device 17, so that the upward-rough-motion operation of the operation microscope 25 for the front lens 74 and the downward-rough-motion operation for the observation using only the operation microscope 25 can be performed using a compact structure.

As described above, the operation microscope 25 anterior to the support arm (second arm 6) of the parallel link type can be roughly moved upward and downward by the first electrically-operated upward-and-downward-motion device 17. Therefore, the operation microscope 25 can be roughly moved promptly and accurately up to a use position of the front lens 74 without providing large drive energy.

When the operation microscope 25 is moved upward by the first electrically-operated upward-and-downward-motion device 17, the operation microscope 25 linearly moves on the same axis in the vertical direction at a position near the observation optical axis. Therefore, the operation microscope 25 can be promptly and accurately moved to the use position of the front lens 74.

The upward-and-downward-rough-motion is not performed on the support arm (second arm 6) of the parallel link type which has a large weight and a long length. Therefore, a vibration or the like in the support arm (second arm 6) of the parallel link type in the upward-and-downward direction and the right-and-left direction, resulting from the upward-rough-motion or the downward-rough-motion during the surgery is not caused. Thus, the operation microscope 25 can be roughly moved upward and downward with a stable state.

As a result, the surgical region or the like can be stably observed without causing any blur immediately after the operation microscope 25 is roughly moved upward and downward, so that the surgery or the like can be promptly restarted immediately after the operation microscope 25 is roughly moved upward and downward.

<Others>

When a mode in which the first and second electrically-operated upward-and-downward-motion devices 17 and 24 are operated so as to move the operation microscope 25 in reverse directions at different speeds is provided, the operation microscope 25 can be super finely moved upward and downward. In this case, when the operating speeds of the first and second electrically-operated upward-and-downward-motion devices 17 and 24 can be controlled, the operation microscope 25 can be finely moved at a speed corresponding to the preference of a user.

MODIFIED EXAMPLE 1

According to the embodiment described above, when the operation signal from the upward-rough-motion switch 30 is inputted, the arithmetic and control circuit 27 controls the first drive motor 18 of the first electrically-operated upward-and-downward-motion device 17 to finely move the support member 19 upward at the speed v1 with respect to the second arm 6. In addition, the arithmetic and control circuit 27 controls the second drive motor 26 of the second electrically-operated upward-and-downward-motion device 24 to finely move the operation microscope 25 upward at the speed v2 with respect to the support bracket 23. As a result, the operation microscope 25 is roughly moved upward at the speed (v1+v2) with respect to the second arm 6. However, the present invention is not limited to such a structure and operation.

That is, when the operation signal from the upward-rough-motion switch 30 is inputted, the arithmetic and control circuit 27 controls the first electrically-operated upward-and-downward-motion device 17 to roughly move the support member 19 upward at a speed V (V>>v1) with respect to the second arm 6. Therefore, the operation microscope 25 can be roughly moved upward by only the first electrically-operated upward-and-downward-motion device 17. In this case, it is unnecessary that the first electrically-operated upward-and-downward-motion device 17 has a function as the micro-motion device.

Because the upward-rough-motion is not performed on the support arm (second arm 6) of the parallel link type which has a large weight and a long length, a vibration or the like in the support arm (second arm 6) of the parallel link type in the upward-and-downward direction, resulting from the upward-rough-motion is not caused. Therefore, the operation microscope 25 can be roughly moved upward with a stable state. This point is the same even in the case of the downward-rough-motion control.

In this case, because the second electrically-operated upward-and-downward-motion device 24 is not operated, the second electrically-operated upward-and-downward-motion device 24 can be made to a state in which a stroke for the upward-and-downward-micro-motion operation in the upward-and-downward direction is left. Thus, after the operation microscope 25 is roughly moved upward and downward by the first electrically-operated upward-and-downward-motion device 17, the operation microscope 25 can be finely moved upward and downward by the second electrically-operated upward-and-downward-motion device 24.

(Embodiment 2)

[Structure]

In Embodiment 2 of the present invention, the rough-motion adjusting mechanism 66 and the micro-motion mechanism 70 which are described in Embodiment 1 of the present invention are omitted. Note that the same references as used in Embodiment 1 of the present invention are provided to the same portions as in Embodiment 1 of the present invention or similar portions thereto and the descriptions are omitted here. In the descriptions related to the operation and the like of the present invention, the members shown in Embodiment 1 of the present invention are used.

Also, in Embodiment 2 of the present invention, as shown in FIGS. 8 to 11A, and 12, a connecting and fixing member 56' is used instead of the connecting and fixing member 56 in Embodiment 1 of the present invention. The lower end portions of the support shafts 54, 54 of the upper arm portion 52 are connected and fixed to each other through the connecting and fixing member 56'. The connecting and fixing member 56' has a support plate portion (support portion) 80 that horizontally protrudes below the housing portion 42. As shown in FIG. 13, a square U-shaped mounting portion 81 that extends backward and downward is integrally formed in a tip portion of the support plate portion 80.

The square U-shaped mounting portion 81 has a front wall 81a and right and left side walls 81b, 81b. The rotation shaft 62 which is integrally provided to the connecting shaft 63 is supported to the side walls 81b, 81b so as to be rotatable. Therefore, the connecting shaft 63 can be rotated at two positions, that is, a position at which it faces downward and a position at which it is along the lower surface of the housing portion 42 by being rotated backward and upward.

In addition to this, as shown in FIG. 13, a washer 63a of the low arm portion 53 and the coil spring 65 are fitted to the connecting shaft 63 in this order. The tip portion of the connecting shaft 63 is screwed into a nut member 82. Therefore, the coil spring 65 is compressed, so that the washer 63a is elastically in contact with the lower surface or the rear surface of the side walls 81b, 81b.

A support arm 83 of the lower arm portion 53 whose axis coincides with that of the connecting shaft 63 is integrally provided to the nut member 82. In addition, an operating lever 84 which is an operating member is integrally provided to the nut member 82. Note that, ultimately, the nut member 82 is integrally provided to the connecting shaft 63 by bonding, welding, or the like.

Figure 14A:
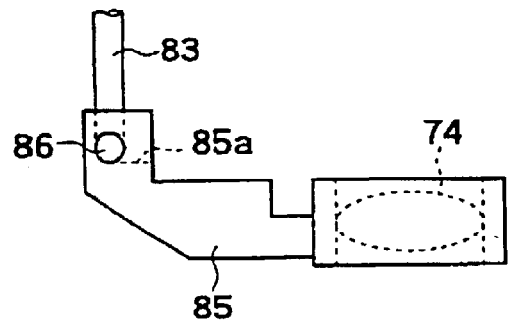
FIG. 14A is an enlarged main part explanatory view showing a lens holding member (85) and FIG. 14B is a plan view of FIG. 14B.
Figure 14B:
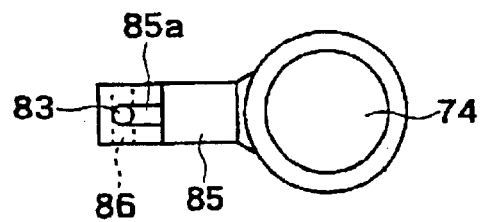

A tip portion of the support arm 83 is placed in a groove 85a of an end of a lens holding member 85. As shown in FIGS. 14A and 14B, the lens holding member 85 is held to the tip portion of the support arm 83 so as to be rotatable forward and backward about a support shaft 86. That is, when the support arm 83 is moved downward, the lens holding member 85 can be held by the support arm 83 so as to become a state in which the lens holding member 85 is perpendicular (vertical) to the support arm 83. In addition, when the support arm 83 is moved so as to be located along the lower surface of the housing portion 42, the lens holding member 85 can be folded along the support arm 83. The front lens 74 is held by the lens holding member 85.

In Embodiment 1 of the present invention, the shaft guide member 50 is fixed to the case main body 24a of the second electrically-operated upward-and-downward-motion device 24. In contrast to Embodiment 1, the shaft guide member 50 is not fixed to the case main body 24a in Embodiment 2 of the present invention. That is, in Embodiment 2 of the present invention, a third electrically-operated upward-anddownward-micro-motion device 90 is mounted to the case main body 24a. Therefore, the shaft guide member 50 can be finely moved upward and downward within a predetermined area by the third electrically-operated upward-and-downward-micro-motion device 90.

Figure 12:
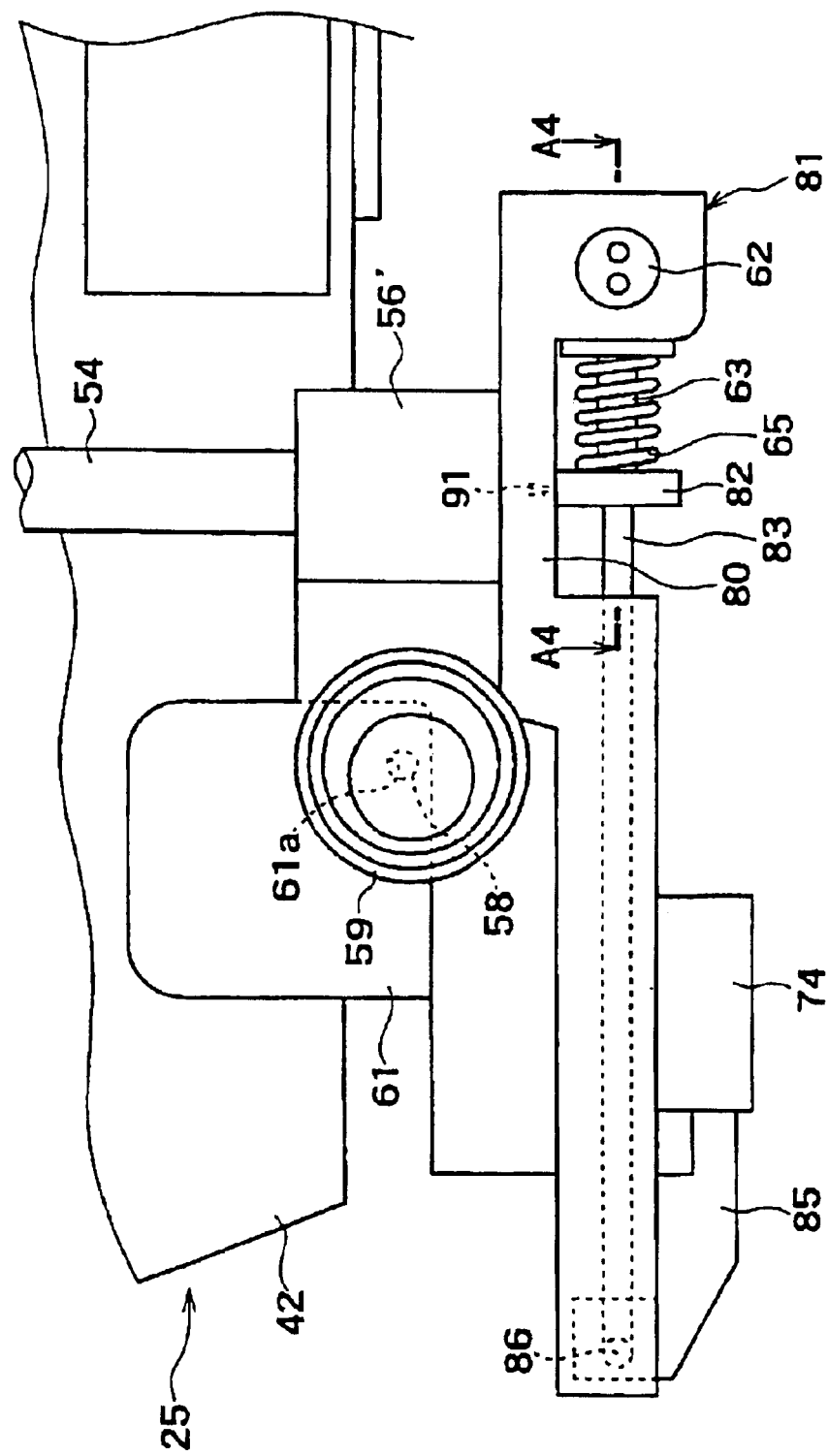
FIG. 12 is an enlarged main part view of FIG. 11A.
Figure 13:
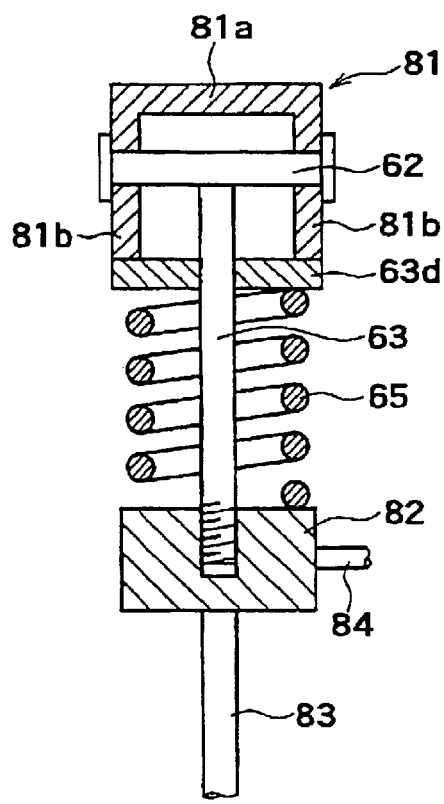
FIG. 13 is a cross sectional view taken along a line A4—A4 shown in FIG. 12.

As shown in FIG. 12, a microswitch 91 for detecting a folding state of the support arm 83 when the support arm 83 is folded along the lower surface of the housing portion 42 is provided as a folding detection unit (storage detection unit) in the support plate portion 80 of the connecting and fixing member 56'.

Figure 15:
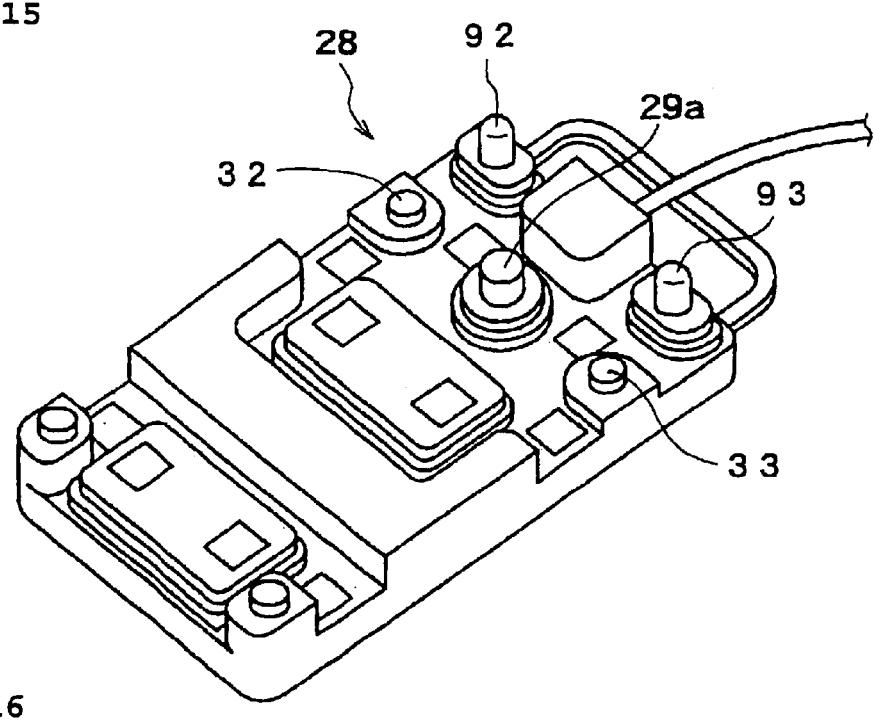
FIG. 15 is an enlarged perspective view showing another example of a foot operation device shown in FIG. 1.

As shown in FIG. 15, upward-rough-motion switch 92 and downward-rough-motion switch 93 are provided on right and left end portions of the foot operation device 28 as another embodiment. A toggle switch is used for each of the switches 92 and 93. In general, the switches 92 and 93 are normally kept to a state in which they are not tilted. The switches 92 and 93 each are tilted right and left to turn ON each contact (not shown).

Figure 9:
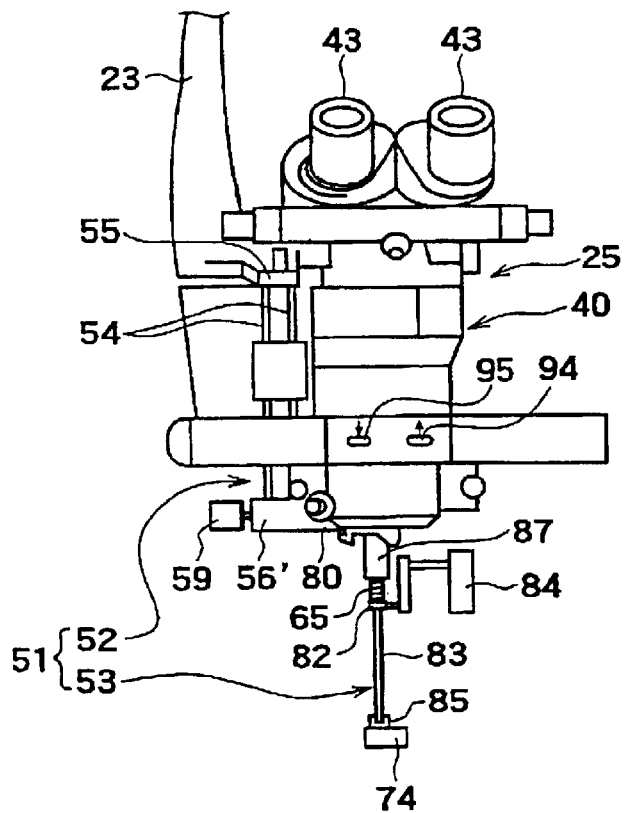
FIG. 9 is a front view showing the operation microscope apparatus shown in FIG. 8.
Figure 10:
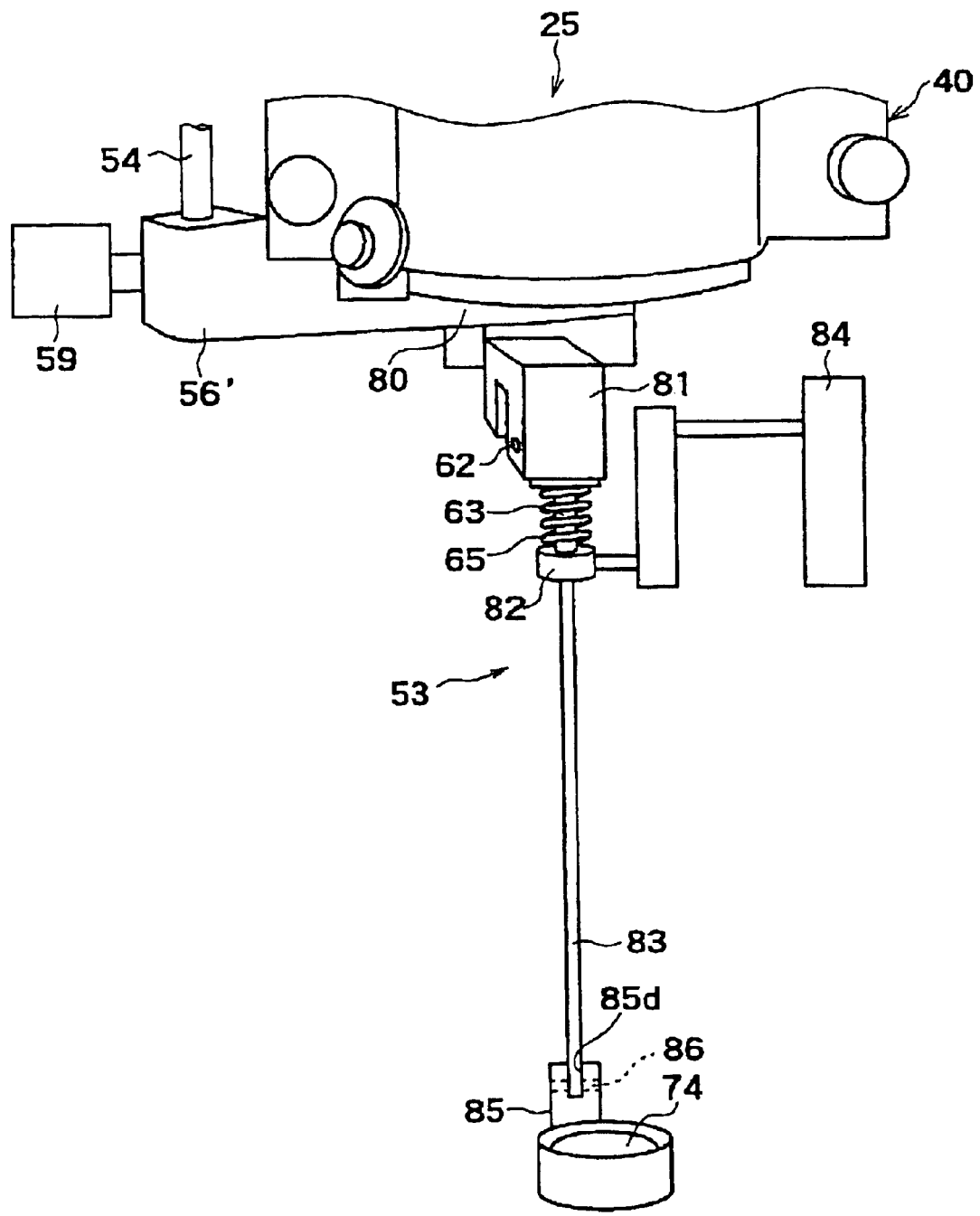
FIG. 10 is an enlarged main part view of FIG. 9.
Figure 11A:
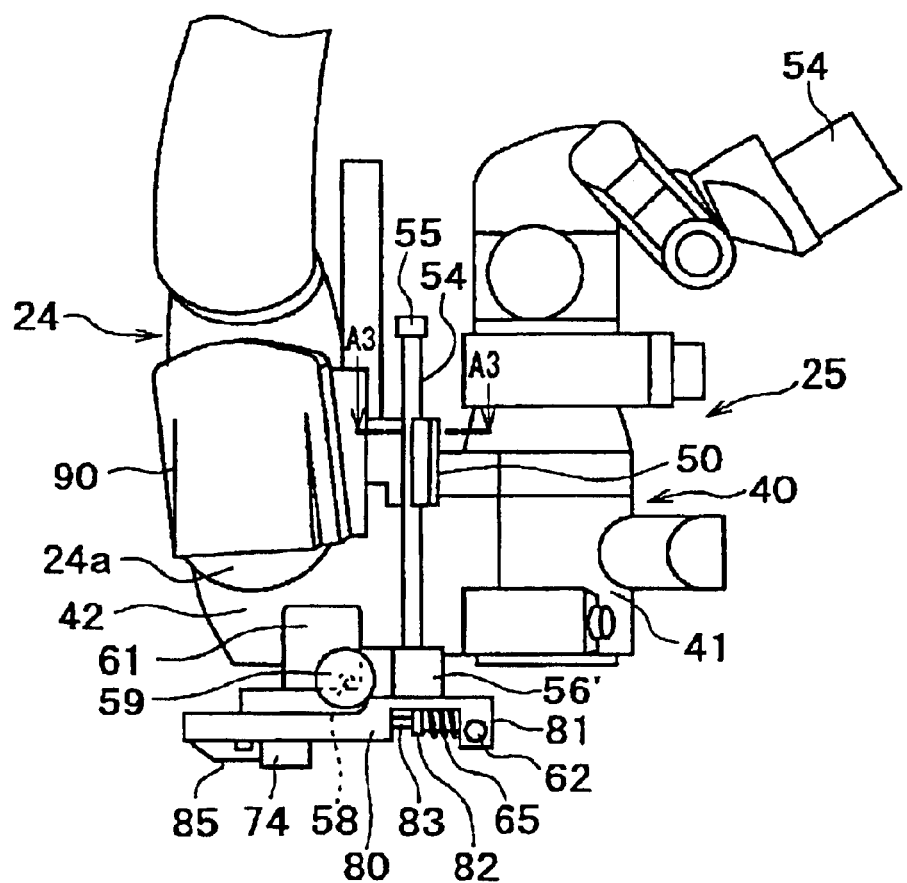
FIG. 11A is a side view in a state in which the lens support arm of the operation microscope apparatus shown in FIG. 8 is folded and FIG. 11B is a cross sectional view taken along a line A3—A3 shown in FIG. 11A.
Figure 11B:
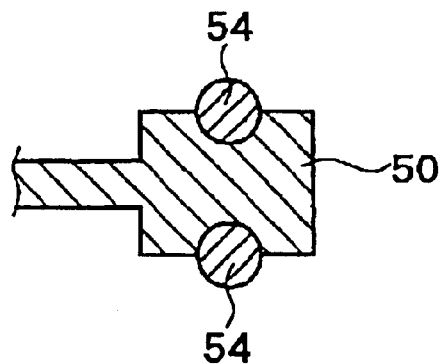

As shown in FIG. 9, an upward-rough-motion switch 94 for operating the first electrically-operated upward-and-downward-motion device 17 to roughly move the operation microscope 25 upward and a downward-rough-motion switch 95 for operating the first electrically-operated upward-and-downward-motion device 17 to roughly move the operation microscope 25 downward are provided in the operation microscope 25. Note that in Embodiment 2 of the present invention, the first electrically-operated upward-and-downward-motion device 17 is used as an electrically-operated rough-motion device.

As shown in FIG. 16, the arithmetic and control circuit 27 is set to control the third electrically-operated upward-and-downward-micro-motion device 90. On/off signals from the microswitch 91, the switches 92 and 93, the upward-rough-motion switch 94, the downward-rough-motion switch 95, and the like are set to be inputted to the arithmetic and control circuit 27.

When the upward-rough-motion switch 94 is pressed in a state in which the microswitch 91 is turned ON, the arithmetic and control circuit 27 operates the first electrically-operated upward-and-downward-motion device 17 to roughly move the operation microscope 25 upward by the predetermined amount (for example, 57 mm). When the downward-rough-motion switch 95 is pressed with the same state, the arithmetic and control circuit 27 operates the first electrically-operated upward-and-downward-motion device 17 to roughly move the operation microscope 25 downward by the predetermined amount (for example, 57 mm). Note that the arithmetic and control circuit 27 is set not to operate the first electrically-operated upward-and-downward-motion device 17 in a state in which the microswitch 91 is turned OFF.

[Operation]

Next, the control operation of the operation microscope apparatus having the above-mentioned structure, which is performed by the arithmetic and control circuit 27 will be described.

<Extension of Lens Support Arm 51 to Use Front Lens>

When the front lens 74 is used in the above-mentioned structure, the lower arm portion 53 of the lens support arm 51 is extended downward to locate the front lens 74 below the objective lens of the observation optical system which is not shown in the microscope main body 40.

That is, the operator operates the operating lever 84 to rotate the support arm 83 downward about the rotation shaft 62 and to elastically have the washer 63a be in contact with the lower surface of the side walls 81b, 81b by the spring force (elastic force) of the coil spring 65, thereby locating the support arm 83 in the upward-and-downward direction. In addition, with the state in which the support arm 83 is located in the upward-and-downward direction, the operator extends the lens holding member 85 held to the tip portion of the support arm 83 in a direction perpendicular to the support arm 83. Thus, the front lens 74 held by the lens holding member 85 is located below the objective lens (not shown) of the operation microscope 25, so that the optical axis of the front lens 74 is made to coincide with the optical axis of the objective lens (not shown).

In such a state, the microswitch 91 is turned OFF.

<When not Using Front Lens by Folding Lens Support Arm 51>

When the front lens 74 is not used in the above-mentioned structure, the lower arm portion 53 of the lens support arm 51 is rotated upward to retreat the front lens 74 upward from below the objective lens of the observation optical system (not shown) in the microscope main body 40.

That is, the operator operates the operating lever 84 to rotate the support arm 83 upward about the rotation shaft 62 and to elastically have the washer 63a be in contact with the rear surface of the side walls 81b, 81b by the spring force (elastic force) of the coil spring 65, thereby locating the support arm 83 along the housing portion 42. In addition, the operator folds the lens holding member 85 held to the tip portion of the support arm 83 along the support arm 83, so that the lens holding member 85 is made to be located along the housing portion 42.

In such a state, the microswitch 91 is turned ON by the nut member 82 integrally provided to the support arm 83. An ON signal is inputted to the arithmetic and control circuit 27, so that the arithmetic and control circuit 27 detects that the lens support arm 51 is folded.

<Rough Position Adjustment of Operation Microscope>

The fixing screw 5 is loosened and the arm portion 4b of the first arm 4 is horizontally rotated, so that the second arm 6 can be roughly turned in the target direction. After the second arm 6 is roughly turned in the target direction by such operation, the fixing screw 5 is tightened to fix (lock) the first arm 4 so as not to horizontally rotate.

In this state, when the fixing screws 7a and 15 are loosened to move the operation microscope 25 from right to left or up and down while holding it, the second arm 6 is horizontally rotated about the rotation shaft (not shown) of the first support member 7 and swung upward and downward. Therefore, the operation microscope 25 can be moved to a target location. In addition, when the fixing screw 21 is loosened, the operation microscope 25 can be rotated together with the support shaft 20b about its axis. Therefore, an orientation of the operation microscope 25 in the horizontal direction can be changed by the rotational operation.

When the operation microscope 25 and the front lens 74 are moved by the above-mentioned operation to a position at which a surgical region can be roughly observed and the fixing screws 7a, 15, and 21 are tightened, the rough position setting of the operation microscope 25 is completed.

In this state, when an operator tilts the joystick 29a of the foot operation device 28, a tilt operation signal from the joystick 29a is inputted to the arithmetic and control circuit 27. The arithmetic and control circuit 27 controls the X-Y micro-motion device 20 to finely move the support shaft 22 in the same direction as the tilt direction of the joystick 29a. Therefore, when the operator tilts the joystick 29a to drive the support shaft 22 in the horizontal direction, the operation microscope 25 supported by the support shaft 22 is finely moved in the horizontal direction. The adjustment is performed such that the entire target surgical region (for example, the anterior segment of the eye to be examined) is located within a field of view of the operation microscope 25. Thus, the rough position adjustment in the horizontal direction (X-Y direction) is conducted.

The rough position adjustment is always conducted regardless of whether the front lens 74 is used or not.

<When Front Lens is Used>

When the front lens 74 is used, the support arm 83 of the lens support arm 51 which is in a folding state is extended so as to be located downward, so that the microswitch 91 is turned OFF. Thus, when the front lens 74 is used, the arithmetic and control circuit 27 does not detect that the support arm 83 is in the folded state by the microswitch 91.

In this state, the arithmetic and control circuit 27 is set not to control the first electrically-operated upward-and-downward-motion device 17 even when the upward-rough-motion switch 94 and the downward-rough-motion switch 95 are operated.

In this state in which the microswitch 91 is turned OFF, when the switch 92 of the foot operation device 28 is operated, that is, when the switch 92 is tilted left or right, the arithmetic and control circuit 27 performs the adjustment such that a width of a slit diaphragm to a slit illumination light flux which is projected from the operation microscope 25 to the observation region such as the eye to be examined becomes larger or smaller.

When the front lens 74 is used, the engaging pin 58 is taken out from the engaging hole 61a of the engaging plate 61 so that the connecting and fixing member 55 of the lens support arm 51 is in contact with the upper end of the shaft guide member 50 by the own weight of the connecting and fixing member 55. Therefore, the lens support arm 51 can follow the upward-and-downward motion of the shaft guide member 50.

When the switch 93 of the foot operation device 28 is operated in the state in which the microswitch 91 is turned OFF, the arithmetic and control circuit 27 controls the third electrically-operated upward-and-downward-micro-motion device 90. Therefore, the shaft guide member 50 is finely moved upward and downward to finely move the entire lens support arm 51 upward and downward, so that the front lens 74 can be finely moved upward and downward with respect to the objective lens (not shown) of the operation microscope 25. Thus, an interval between the front lens 74 and the objective lens can be adjusted.

When the operation signal from the upward-micro-motion switch 32 is inputted, the arithmetic and control circuit 27 controls the second drive motor 26 of the second electrically-operated upward-and-downward-motion device 24 to finely move the operation microscope 25 upward with respect to the front lens 74. When the operation signal from the downward-micro-motion switch 33 is inputted, the arithmetic and control circuit 27 controls the second drive motor 26 of the second electrically-operated upward-and-downward-motion device 24 to finely move the operation microscope 25 downward with respect to the front lens 74.

With the upward-and-downward motion of the operation microscope 25, the front lens 74 is finely moved integrally with the operation microscope 25 upward and downward while an interval with the objective lens of the operation microscope 25 is kept constant.

Therefore, the operator selectively operates the upward-micro-motion switch 32 and the downward-micro-motion switch 33 to finely move the operation microscope 25 and the front lens 74 upward and downward integrally. Thus, the focusing operation of the operation microscope 25 to the observation region (surgical region) can be performed. Then, in the state in which the focusing operation has been performed, the operator conducts the surgery while observing the surgical region by using the operation microscope 25.

<When Front Lens is not Used>

When the front lens 74 is not used, the engaging pin 58 is inserted into the engaging hole 61a of the engaging plate 61. In addition, when the front lens 74 is not used, the support arm 83 is folded backward along the lower surface of the housing portion 42 and the lens holding member 85 is made to be folded along the support arm 83 and the lower surface of the housing portion 42.

When the support arm 83 of the lens support arm 51 is folded upward and the front lens 74 is not used, the microswitch 91 is turned ON. Thus, the arithmetic and control circuit 27 detects that the support arm 83 is in the folding state by the microswitch 91.

In the state in which the folding state of the support arm 83 is detected by the microswitch 91, when the switch 92 is tilted left or right, the arithmetic and control circuit 27 controls the amount of light from a light source of an illumination optical system in the housing portion 42.

When the switch 93 is tilted left or right, on/off control of the light source of the illumination optical system in the housing portion 42 is performed.

In a state in which the support member 19 is moved to a lower end by the first electrically-operated upward-and-downward-motion device 17 and the folding state of the support arm 83 is detected by the microswitch 91, when the upward-rough-motion switch 94 provided to the operation microscope 25 is turned ON, the arithmetic and control circuit 27 operates the first electrically-operated upward-and-downward-motion device 17 to roughly move upward the second electrically-operated upward-and-downward-motion device 24 and the operation microscope 25 which are supported by the support member 19 through the plurality of members by the predetermined amount. Therefore, the operation microscope 25 and the front lens 74 are located at the retreat position.

In a state in which the support member 19 is moved to an upper end by the first electrically-operated upward-and-downward-motion device 17 and the folding state of the support arm 83 is detected by the microswitch 91, when the downward-rough-motion switch 95 provided to the operation microscope 25 is turned ON, the arithmetic and control circuit 27 operates the first electrically-operated upward-and-downward-motion device 17 to roughly move the second electrically-operated upward-and-downward-motion device 24 and the operation microscope 25 downward by the predetermined amount. Therefore, the operation microscope 25 and the front lens 7 are returned from the retreat position to the use position.

As described above, when the operation microscope 25 is roughly moved upward and downward by the first electrically-operated upward-and-downward-motion device 17, the operation microscope 25 straightly moves on the same axis in the vertical direction. Therefore, the operation microscope 25 can be roughly moved between the retreat position and the use position with accuracy.

In a state in which the support arm 83 of the lens support arm 51 is folded upward and the engaging pin 58 is inserted into the engaging hole 61a of the engaging plate 61, when the operation signal from the upward-micro-motion switch 32 is inputted, the arithmetic and control circuit 27 controls the second drive motor 26 of the second electrically-operated upward-and-downward-motion device 24 to finely move the operation microscope 25 and the front lens 74 upward integrally.

In a state in which the support arm 83 of the lens support arm 51 is folded upward and the engaging pin 58 is inserted into the engaging hole 61a of the engaging plate 61, when the operation signal from the downward-micro-motion switch 33 is inputted, the arithmetic and control circuit 27 controls the second drive motor 26 of the second electrically-operated upward-and-downward-motion device 24 to finely move the operation microscope 25 and the front lens 74 downward integrally.

Therefore, in the state in which the operation microscope 25 and the front lens 74 are returned from the retreat position to the use position, the operator alternately operates the upward-micro-motion switch 32 and the downward-micro-motion switch 33 to finely move the operation microscope 25 and the front lens 74 upward and downward integrally. Thus, the focusing operation of the operation microscope 25 to the observation region (surgical region) can be performed with the state in which the front lens 74 is not used. Then, in a state in which the focusing operation has been performed, the operator conducts the surgery while observing the surgical region by using the operation microscope 25.

<Setting for Upward-rough-motion of Front Lens to Use Position>

When the support arm 83 of the lens support arm 51 is folded along the lower surface of the housing portion 42 and the tip portion of the engaging pin 58 is inserted into the engaging hole 61a, the lens support arm 51 and the front lens 74 are made in the storage state and the front lens 74 is made in a state in which it is not used. With such states, the surgery of the eye to be examined or the like is conducted in some cases. In such states, the operation microscope 25 is located at a position closer to the eye to be examined as compared with the case where the front lens 74 is used. Therefore, when the surgery with the above-mentioned states is changed into the surgery using the front lens 74, the following setting for controlling the first electrically-operated upward-and-downward-motion device 17 is also possible.

That is, in the state in which the support member 19 is moved to a lower end by the first electrically-operated upward-and-downward-motion device 17 and the folding state of the support arm 83 is detected by the microswitch 91, when the upward-rough-motion switch 94 provided to the operation microscope 25 is turned ON, the arithmetic and control circuit 27 operates the first electrically-operated upward-and-downward-motion device 17 to roughly move upward the second electrically-operated upward-and-downward-motion device 24 and the operation microscope 25 which are supported by the support member 19 through the plurality of members with respect to the front lens 74 by the predetermined amount. In this time, the amount of upward-rough-motion of the operation microscope 25 is the amount (stroke) that the support arm 83 of the lens support arm 51 can be extended downward to locate the front lens 74 below the objective lens (not shown) of the operation microscope 25.

Also, in the state in which the support member 19 is moved to an upper end by the first electrically-operated upward-and-downward-motion device 17 and the folding state of the support arm 83 is detected by the microswitch 91, when the downward-rough-motion switch 95 provided to the operation microscope 25 is turned ON, the arithmetic and control circuit 27 operates the first electrically-operated upward-and-downward-motion device 17 to roughly move the second electrically-operated upward-and-downward-motion device 24 and the operation microscope 25 downward by the predetermined amount. Thus, the operation microscope 25 is returned to a position at which the observation region (surgery region) such as the eye to be examined can be observed without using the front lens 74.

According to the setting, when the surgery which is conducted using the operation microscope 25 without using the front lens 74 while the observation region (surgical region) such as the eye to be examined is observed is changed into the surgery using the front lens 74, the upward-rough-motion switch 94 may be pressed with the state in which the support arm 83 is folded along the housing portion 42 and the microswitch 91 is turned ON. Thus, the arithmetic and control circuit 27 controls the first electrically-operated upward-and-downward-motion device 17 to roughly move the X-Y micro-motion device 20, the support shaft 22, the support bracket 23, the second electrically-operated upward-and-downward-motion device 24, and the operation microscope 25 upward integrally by the predetermined amount, so that the lens support arm 51 can be extended downward. By this extension, the front lens 74 is located below the objective lens (not shown) of the operation microscope 25, with the result that the surgery can be conducted while the observation region (surgical region) such as the eye to be examined is observed using the operation microscope 25 and the front lens 74.

When the eye to be examined is observed using the operation microscope 25 without using the front lens 74 while the front lens 74 is used, the downward-rough-motion switch 95 may be pressed with the state in which the support arm 83 is folded along the housing portion 42 and the microswitch 91 is turned ON. Thus, the arithmetic and control circuit 27 controls the first electrically-operated upward-and-downward-motion device 17 to roughly move the X-Y micro-motion device 20, the support shaft 22, the support bracket 23, the second electrically-operated upward-and-downward-motion device 24, and the operation microscope 25 downward integrally by the predetermined amount. Therefore, the surgery can be conducted while the observation region (surgical region) such as the eye to be examined is observed using only the operation microscope 25. Note that, when the tip portion of the engaging pin 58 is inserted into the engaging hole 61a before the downward-rough-motion operation, the lens support arm 51 and the front lens 74 are made in the storage state and the front lens 74 is made in the state in which it is not used.

According to such structure, a stroke produced in the upward-rough-motion operation or the downward-rough-motion operation to the X-Y micro-motion device 20, the support shaft 22, the support bracket 23, the second electrically-operated upward-and-downward-motion device 24, the operation microscope 25, and the like becomes smaller than a stroke produced at a time when they are more substantially retreated or returned. As a result, a small size device can be used as the first electrically-operated upward-and-downward-motion device 17, so that the upward-rough-motion operation of the operation microscope 25 for the front lens 74 and the downward-rough-motion operation for the observation using only the operation microscope 25 can be performed with a compact structure.

As described above, the operation microscope 25 anterior to the support arm (second arm 6) of the parallel link type can be roughly moved upward and downward by the first electrically-operated upward-and-downward-motion device 17. Therefore, the operation microscope 25 can be roughly moved promptly and accurately up to the use position of the front lens 74 without consuming large drive energy.

When the operation microscope 25 is moved upward by the first electrically-operated upward-and-downward-motion device 17, the operation microscope 25 straightly moves at a position near the observation optical axis on the same axis in the vertical direction. Therefore, the operation microscope 25 can be promptly and accurately moved to the use position of the front lens 74.

The upward-and-downward-rough-motion is not performed on the support arm (second arm 6) of the parallel link type which has a large weight and a long length. Therefore, a vibration or the like in the support arm (second arm 6) of the parallel link type in the upward-and-downward direction and the right-and-left direction, which results from the upward-rough-motion or the downward-rough-motion during the surgery, is not caused. Thus, the operation microscope 25 can be roughly moved upward and downward with a stable state. As a result, the surgical region or the like can be stably observed without shaking immediately after the operation microscope 25 is roughly moved upward and downward, so that the surgery or the like can be promptly restarted immediately after the operation microscope 25 is roughly moved upward and downward.

As described above, the operation microscope apparatus according to the embodiment of the present invention includes: the microscope support portion (support bracket 23 in the second arm 6 side); the operation microscope 25 having the objective lens; the electrically-operated elevating device (second electrically-operated upward-and-downward-motion device 24) that supports the operation microscope 25 to the microscope support portion (support bracket 23) so as to be movable upward and downward; the lens support arm 51 which has the upper arm portion 52 that extends upward and downward and which is supported to the arm support portion (case main body 24a) in the microscope support portion (support bracket 23) side and the lower arm portion 53 whose end is held to the lower end of the upper arm portion 52 so as to be foldable in a direction along the upper arm portion 52; and the front lens 74 held to the other end of the lower arm portion 53. The lower arm portion 53 has the bent arm portion (support arm 73) which is placed below the operation microscope 25 to locate the front lens 74 below the objective lens when the lower arm portion 53 is extended downward. The upper arm portion 52 is held to the arm support portion (case main body 24a) so as to be movable upward and downward within a predetermined area. The engaging portion (engaging hole 61a) is provided in the side portion of the operation microscope 25. The member to be engaged (engaging pin 58) which is engaged with the engaging portion (engaging hole 61a) at a position in which the lower end of the upper arm portion 52 is moved upward to the vicinity of the lower end portion of the operation microscope 25 is provided in the upper arm portion 52.

According to the structure, in the state in which the member to be engaged (engaging pin 58) of the upper arm portion 52 is not engaged with the engaging portion (engaging hole 61a), the upper arm portion 52 of the lens support arm 51 becomes the state in which it can be moved upward and downward relative to the electrically-operated elevating device (second electrically-operated upward-and-downward-motion device 24) and the operation microscope 25. Therefore, in this state, when the electrically-operated elevating device (second electrically-operated upward-and-downward-motion device 24) is operated to move the operation microscope 25 upward and downward, the operation microscope 25 can be moved upward and downward relative to the lens support arm 51 and the front lens 74. Thus, the interval between the objective lens of the operation microscope 25 and the front lens 74 can be adjusted by the electrically-operated elevating device (second electrically-operated upward-and-downward-motion device 24).

Also, when the member to be engaged (engaging pin 58) of the upper arm portion 52 is engaged with the engaging portion (engaging hole 61a) at a position in which the lower end of the upper arm portion 52 is moved upward to the vicinity of the lower end portion of the operation microscope 25 by folding the lower arm portion 53 of the lens support arm 51 upward in the direction along the upper arm portion 52, the lens support arm 51 that supports the front lens 74 can be retreated to an optimum position. That is, a state in which the lens support arm 51 hardly protrudes from the lower end of the operation microscope 25 can be obtained. Therefore, when the front lens 74 is unnecessary, the lens support arm 51 and the front lens 74 can be prevented from hindering the surgery or the like.

In such a state, when the electrically-operated elevating device (second electrically-operated upward-and-downward-motion device 24) is operated to move the operation microscope 25 upward and downward, the operation microscope 25 can be moved integral with the lens support arm 51 and the front lens 74 upward and downward. Therefore, when the operation microscope 25 is maximally moved upward by the electrically-operated elevating device (second electrically-operated upward-and-downward-motion device 24), the operation microscope 25 can be retreated to an optimum position in a state in which the lens support arm 51 and the front lens 74 are folded.

Also, the operation microscope apparatus according to the embodiment of the present invention includes: the operation microscope 25 supported to the pillar 3 through the electrically-operated elevating device for rough-motion (first electrically-operated upward-and-downward-motion device 17); the lens support arm 51 supported to the support portion of the operation microscope so as to be movable between the use position at which the lens support arm is extended downward and the storage position at which the lens support arm is stored upward; the front lens 74 held by the lens supported arm; a control unit (arithmetic and control circuit 27) for controlling the electrically-operated elevating device; and switches (30 and 31; 94 and 95) for upward-and-downward-rough-motion. A detection unit (microswitch 91) for detecting the storage state of the lens support arm 51 to output a detection signal is provided in the operation microscope apparatus. Only when the detection signal of the storage state is received, the control unit (arithmetic and control circuit 27) controls the electrically-operated elevating device (first electrically-operated upward-and-downward-motion device 17) in accordance with the operation of the switches (30 and 31; 94 and 95) to allow the operation microscope 25 to roughly move upward and downward.

According to the structure, the operation microscope 25 can be roughly moved upward and downward with the state in which safety is sufficiently ensured.

Also, in the operation microscope apparatus according to this embodiment of the present invention, the lens support arm 51 is supported to the support portion (case main body 24a) so as to be movable upward and downward within a predetermined area. The engaging member (engaging pin 58) that engages the lens support arm 51 with the operation microscope 25 at the storage position is provided.

According to the structure, the lens support arm 51 and the front lens 74 can be roughly operated integral with the operation microscope 25 upward and downward with the state in which the lens support arm 51 and the front lens 74 are stored.

Because the structure as described above is used, according to the present invention, the operation microscope 25 can be roughly moved upward and downward with the state in which safety is sufficiently ensured.

What is claimed is:

1. An operation microscope apparatus comprising:

an operation microscope supported by a pillar through an electrically-operated elevating device;

a lens support arm supported by a support portion of the operation microscope so as to be movable between a use position at which the lens support arm is extended downward and a storage position at which the lens support arm is stored upward;

a front lens held by the lens support arm;

control means for controlling the electrically-operated elevating device;

a switch for upward-and-downward rough-motion; and detection means for detecting a storage state of the lens support arm to output a detection signal, wherein only when the detection signal of the storage state is received, the control means controls the electrically-operated elevating device by operating the switch to allow the operation microscope to move upward and downward.

2. An operation microscope apparatus according to claim 1, wherein the lens support arm is supported by the support portion so as to be movable upward and downward within a predetermined area.

3. An operation microscope apparatus according to claim 1 or 2, further comprising engaging means for engaging the lens support arm with the operation microscope at the storage position.

* * * * *